US008641876B2

(12) United States Patent
Chen

(10) Patent No.: US 8,641,876 B2
(45) Date of Patent: Feb. 4, 2014

(54) NANOPORE ARRAY STRUCTURED DEVICES FOR BIOSENSING AND ENERGY STORAGE

(75) Inventor: Ellen Tuanying Chen, Germantown, MD (US)

(73) Assignee: Ellen T. Chen, Germantown, MD (US)

( * ) Notice: Subject to any disclaimer, the term of this patent is extended or adjusted under 35 U.S.C. 154(b) by 14 days.

(21) Appl. No.: 13/373,576

(22) Filed: Nov. 21, 2011

(65) Prior Publication Data

US 2012/0193243 A1 Aug. 2, 2012

Related U.S. Application Data

(63) Continuation-in-part of application No. 11/785,660, filed on Apr. 19, 2007, now Pat. No. 8,083,926.

(60) Provisional application No. 60/792,902, filed on Apr. 19, 2006.

(51) Int. Cl.
*G01N 27/327* (2006.01)

(52) U.S. Cl.
USPC ................. 204/403.01; 204/403.06; 977/920; 977/924; 977/948; 977/959

(58) Field of Classification Search
USPC ............ 204/403.01–403.15; 205/777.5, 778, 205/792; 600/309–367; 977/920, 924, 962; 422/502, 603
See application file for complete search history.

(56) References Cited

U.S. PATENT DOCUMENTS

| 5,633,368 | A | * | 5/1997 | Hirsenkorn | .................... 536/103 |
| 5,904,929 | A | * | 5/1999 | Uekama et al. | ................ 424/443 |
| 6,582,583 | B1 | * | 6/2003 | Chen | ............................. 205/317 |
| 2002/0192413 | A1 | * | 12/2002 | Wood et al. | ................... 428/35.7 |

* cited by examiner

*Primary Examiner* — Keith D. Hendricks
*Assistant Examiner* — Susan D Leong

(57) ABSTRACT

The present invention provides a novel device for biosensing and energy storage. The present invented device comprises an electrode having a nanopore structured and bio-communicationally active cyclodextrin attached thereto. The device has demonstrated robust analytical performances for direct single subtype breast cancer measurements without mediators, or native enzyme, and without antibodies labeling; the device is capable to store energy by direct bio-communication with the living cancer cells at real time is demonstrated. It is beneficial in the health care diagnostic applications.

19 Claims, 40 Drawing Sheets

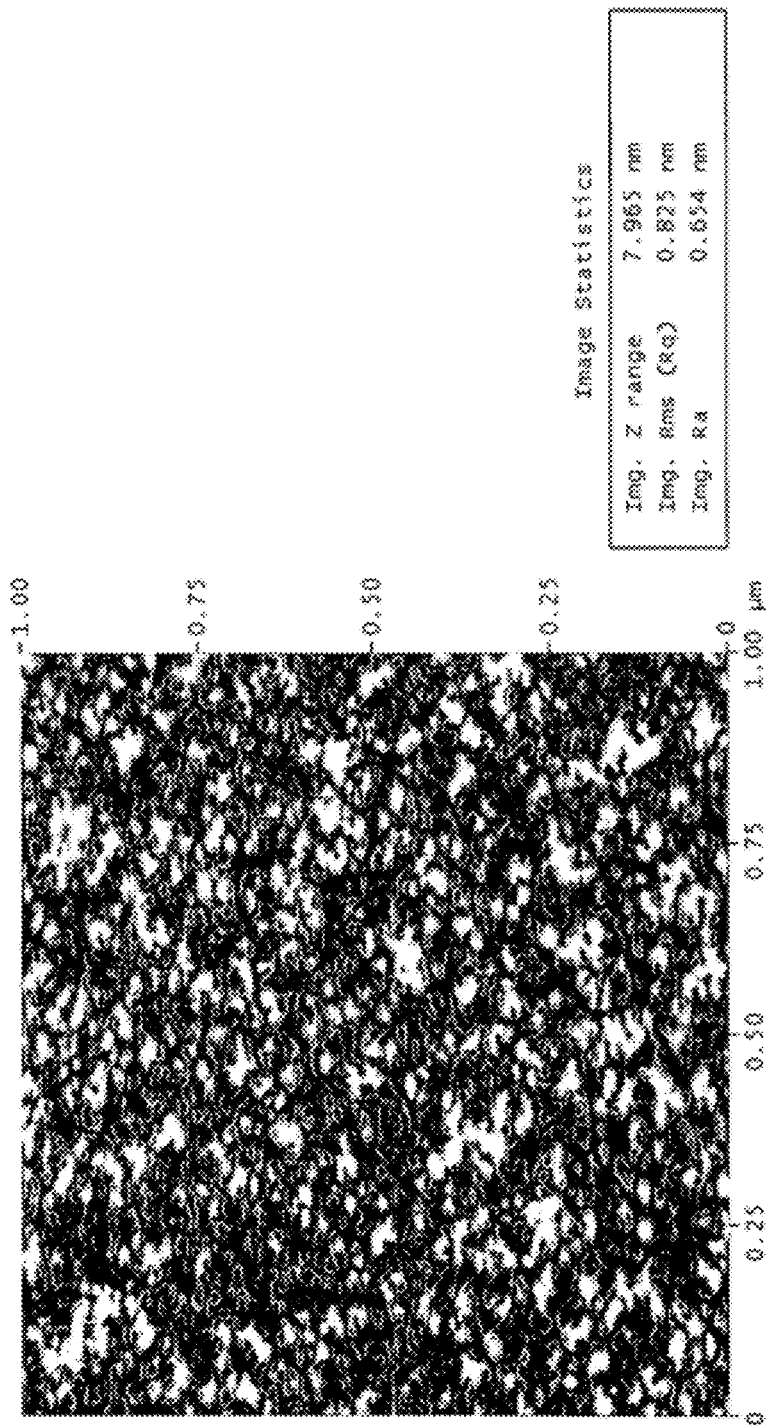

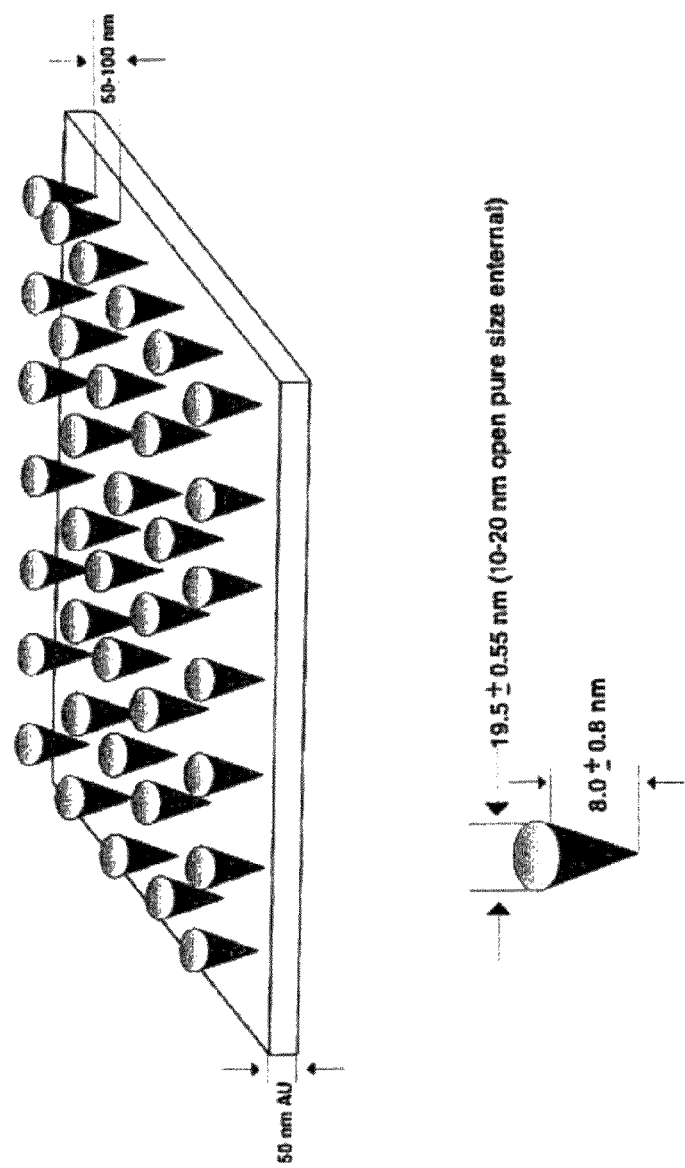

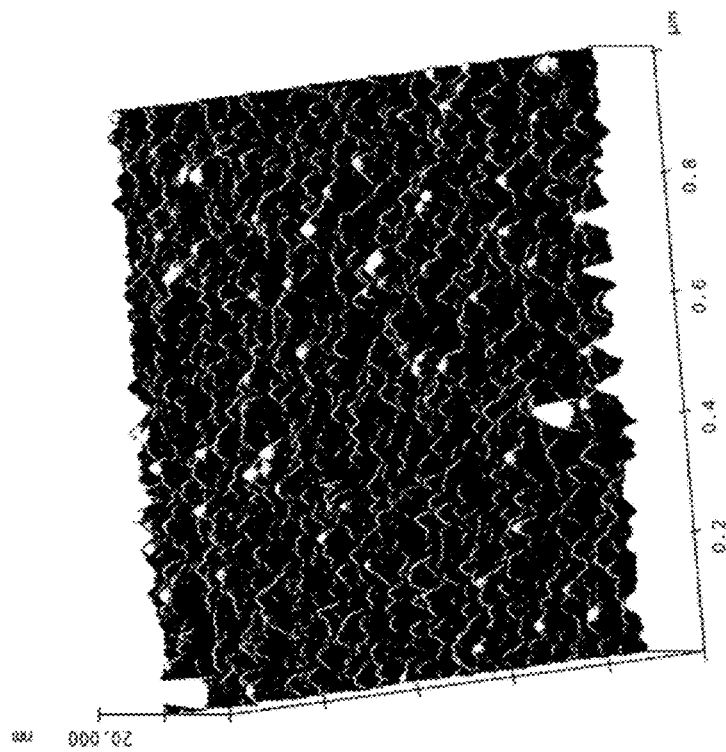

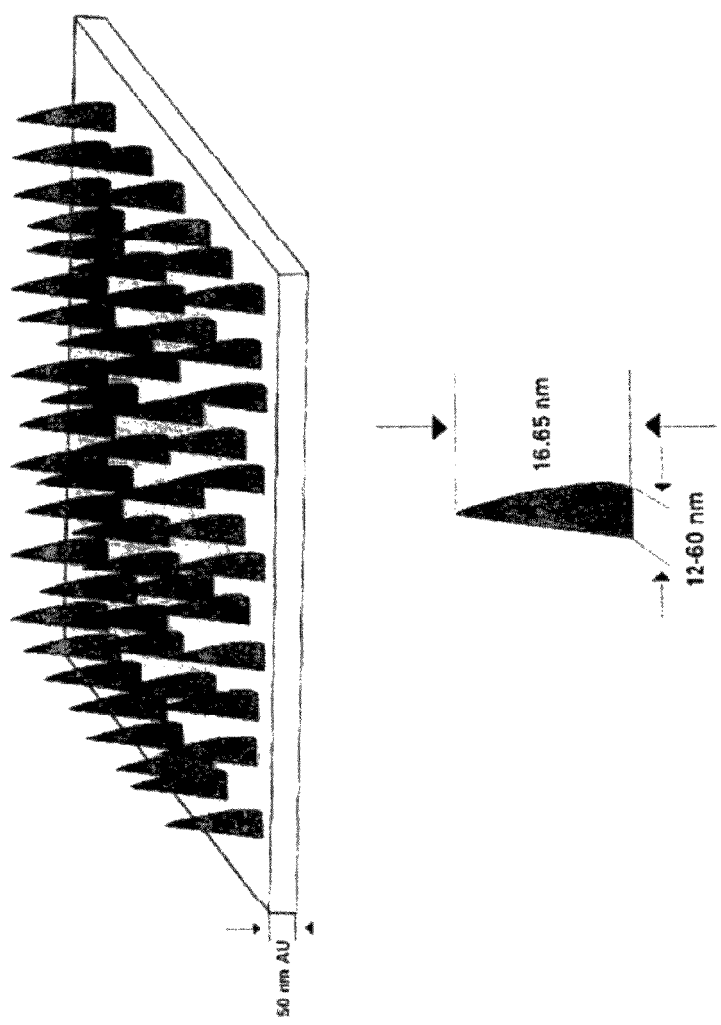

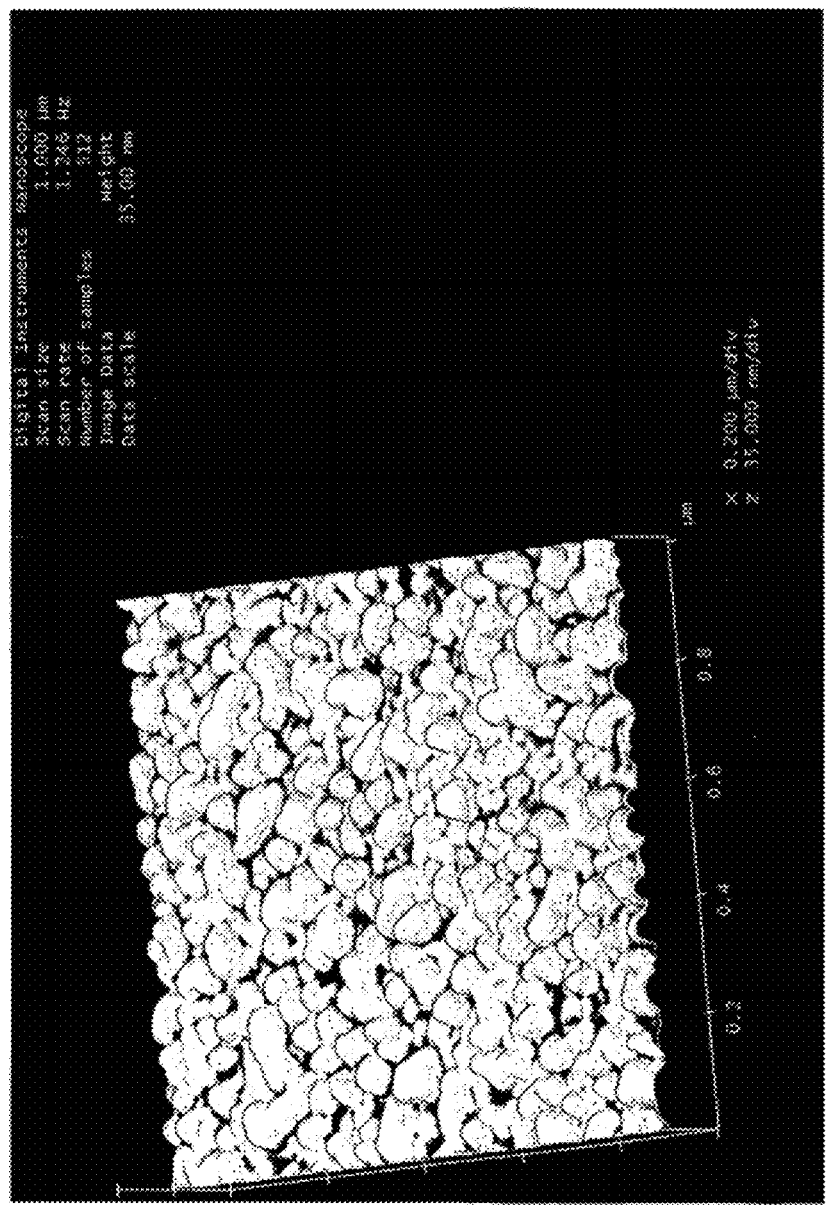

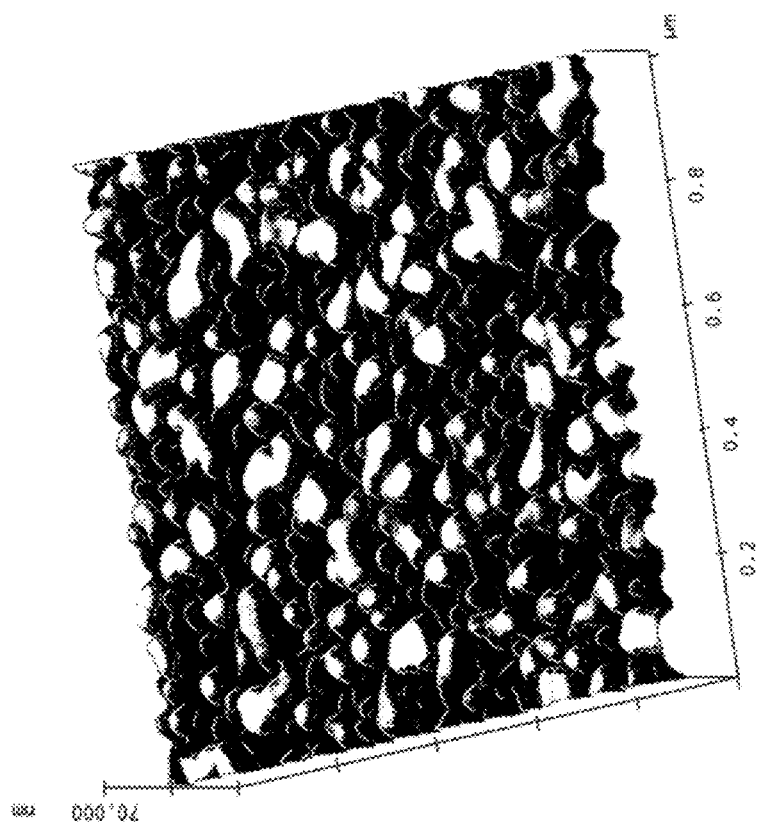

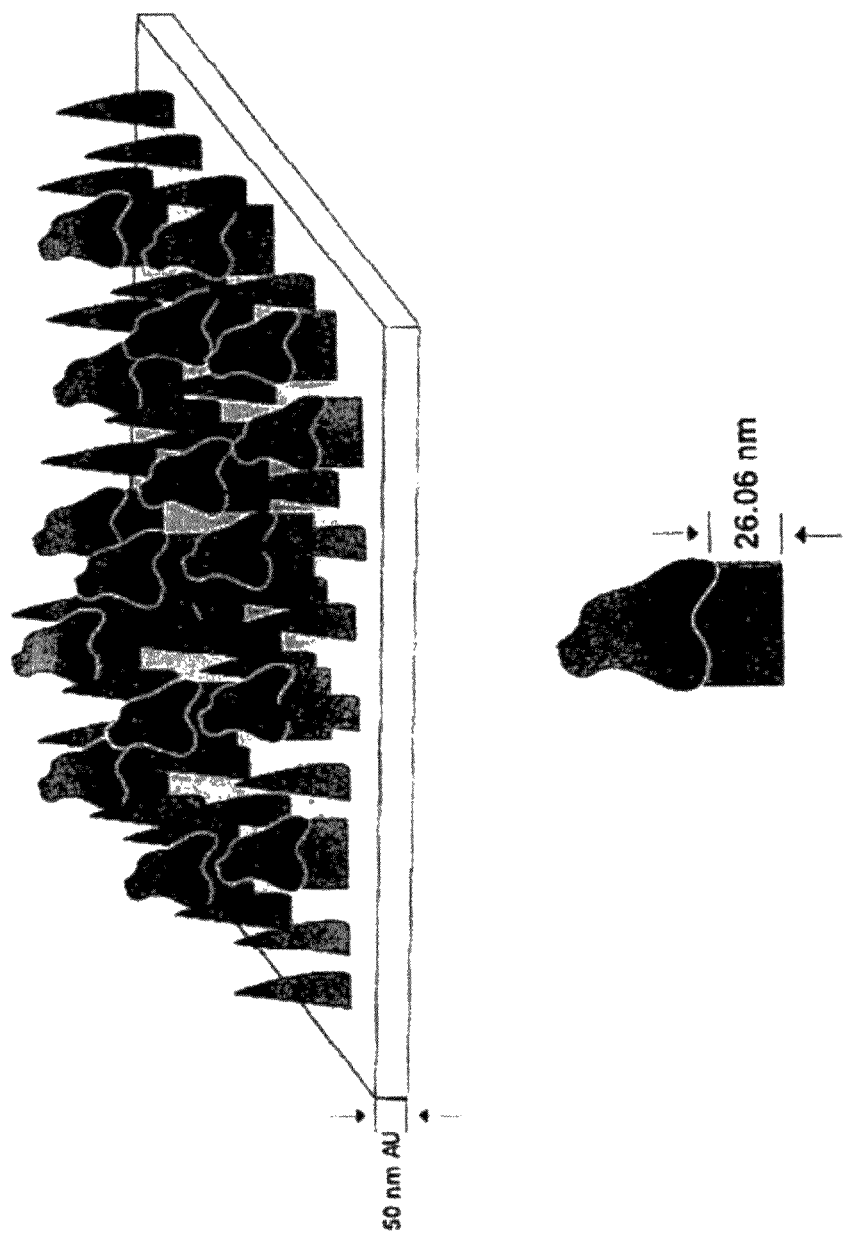

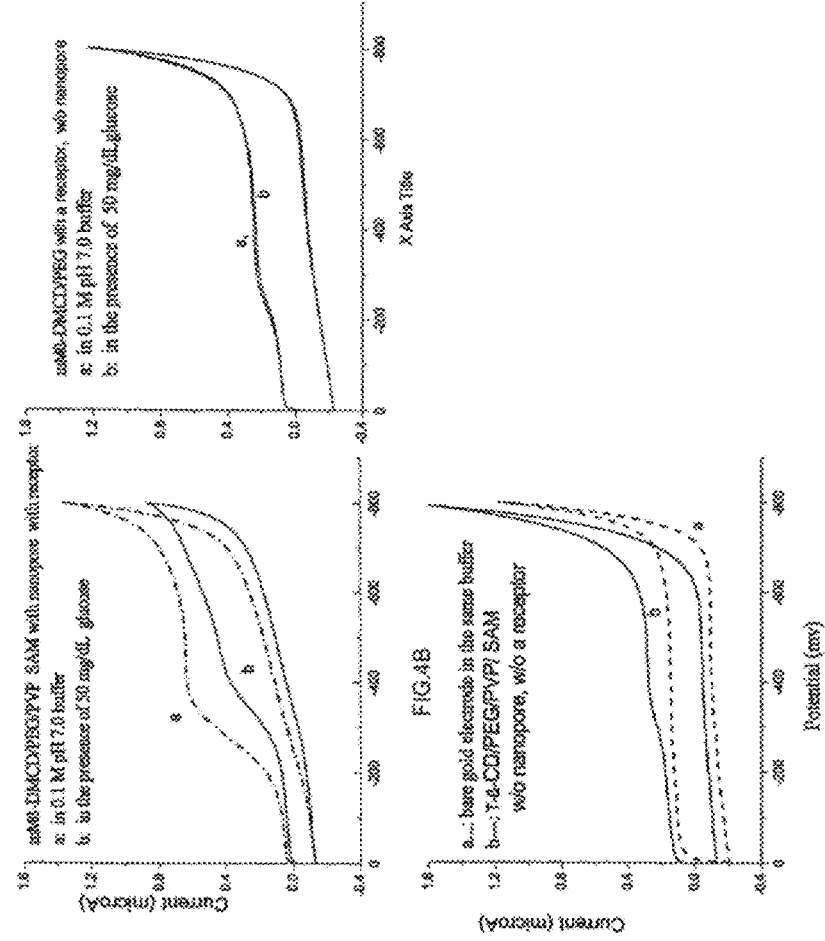

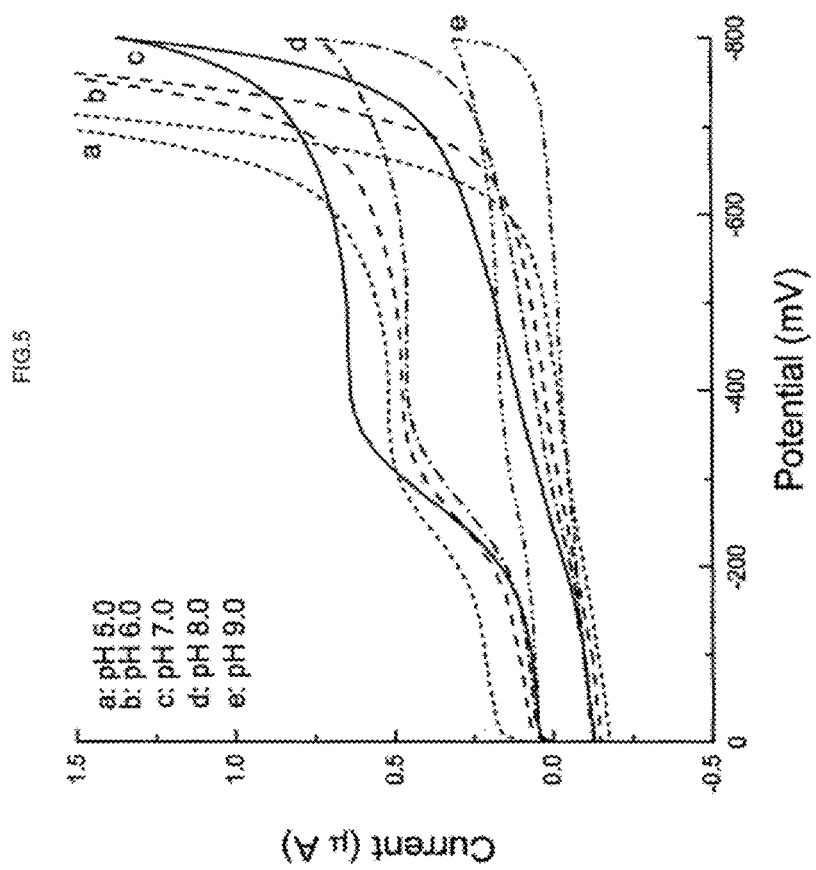

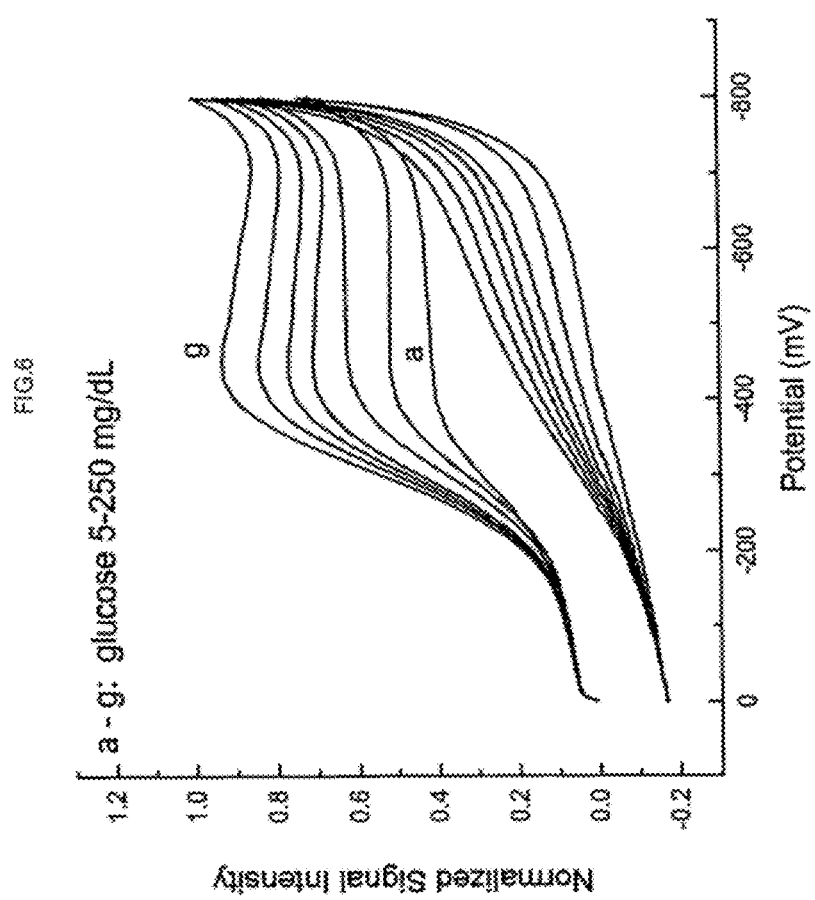

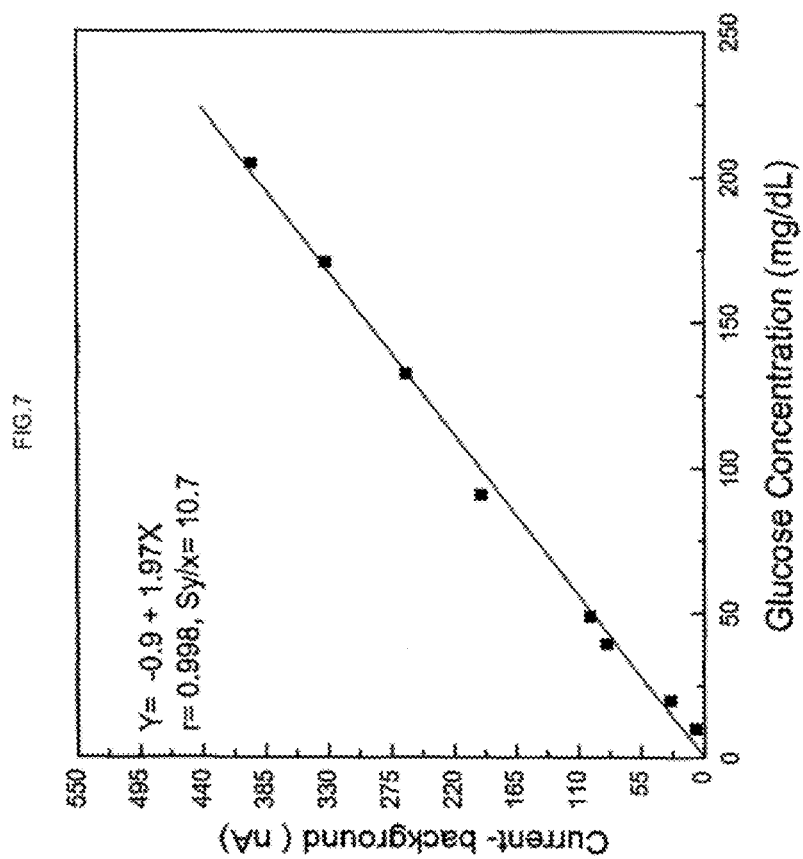

FIG.11
mM-β-DMCD
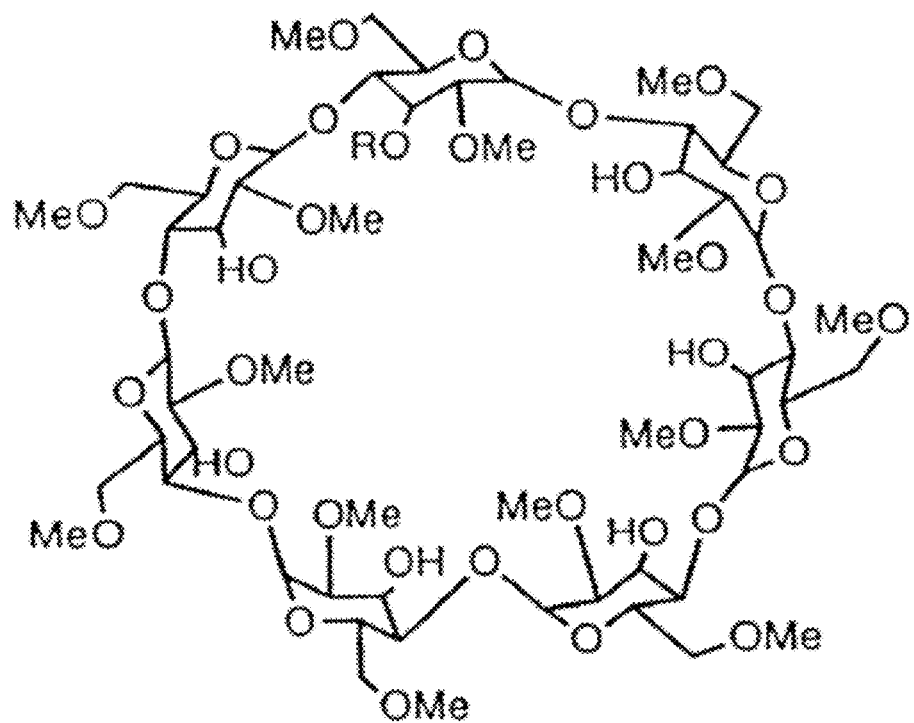
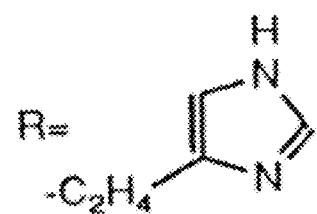

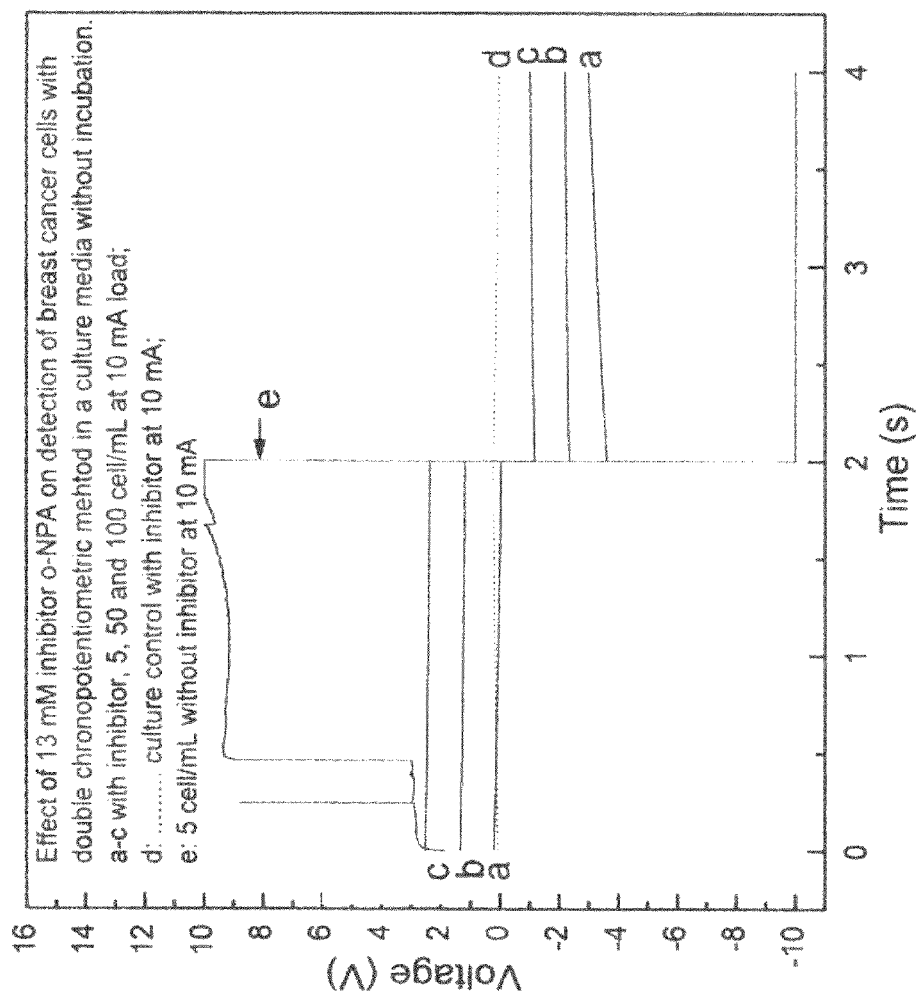

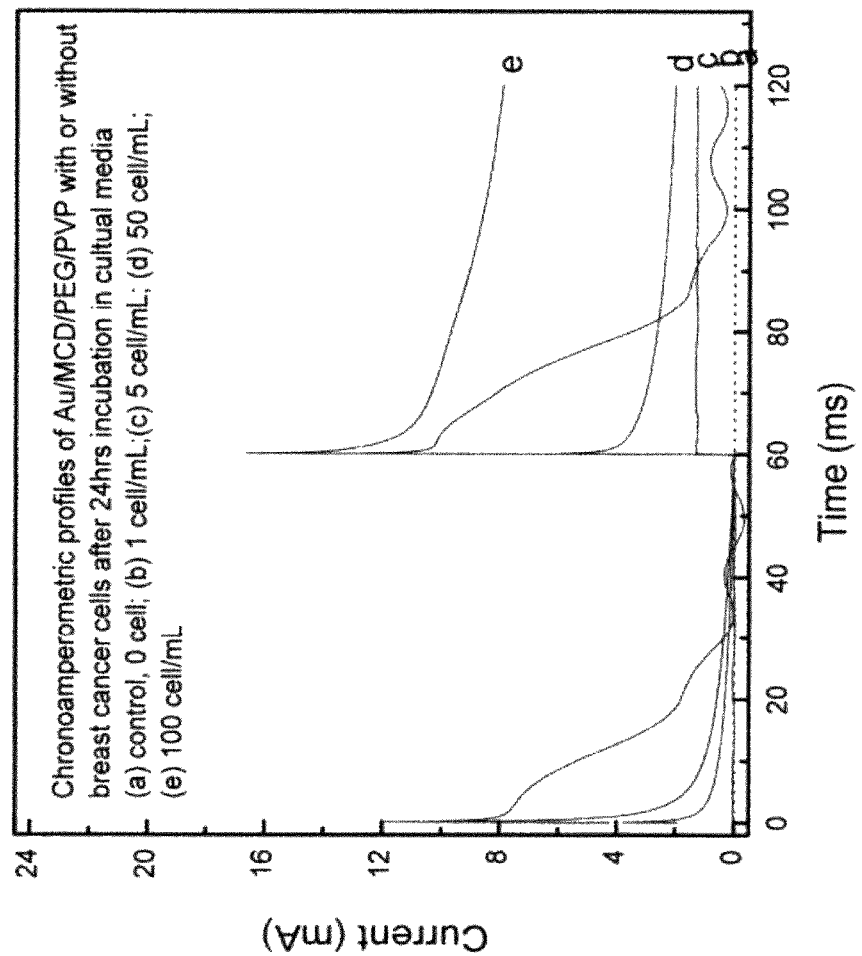

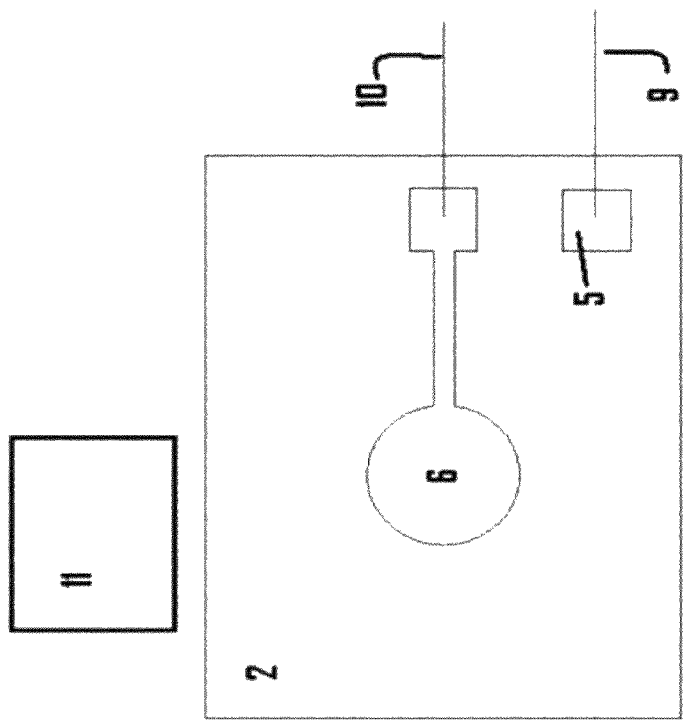
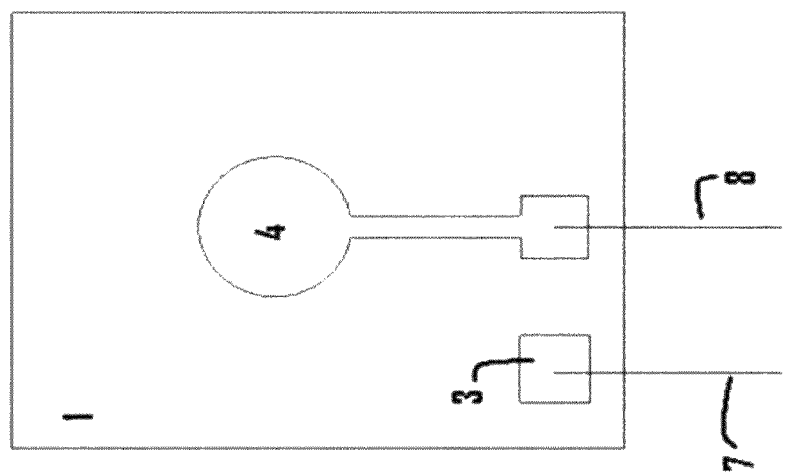
FIG. 22B

US 8,641,876 B2

NANOPORE ARRAY STRUCTURED DEVICES FOR BIOSENSING AND ENERGY STORAGE

CROSS-REFERENCE TO RELATED APPLICATIONS

This patent application claims the benefit of U.S. patent application Ser. No. 11/785,660 filed on Apr. 19, 2007, is a continuation in part application, that claims benefit of U.S. Provisional Patent Application Ser. No. 60/792,902 filed Apr. 19, 2006. The entire disclosure of the prior Patent Application Ser. No. 60/792,902 is hereby incorporated by reference, as is set forth herein in its entirety.

STATEMENT REGARDING FEDERAL RESEARCH

This invention was made with government support through the U.S. Department of health and Human Services, U.S. Food and Drug Administration. The United States Government has certain rights in this invention.

FIELD OF THE INVENTION

The present invention relates to the field of biosensors and, in particular, to biosensors comprising a catalytically active cyclodextrin in a nanopore form.

BACKGROUND OF THE INVENTION

Monitoring blood glucose levels regularly is very important in proper diabetes management, especially for children with type I diabetes. The conventional glucose sensor technologies have limited the development of glucose sensors, especially in its measurements of blood glucose in the hypoglycemia range (see reference 23). The third generation glucose sensors based on DET phenomena were widely reported (see references 6-8). The third generation biosensors for direct glucose measurements are based on an intriguing phenomenon known for the last decade as the bioelectrocatalysis with the direct electron transfer (DET) between the electrode and the redox active sites of bio molecules (see references 1-5). Direct measurement of analyte without using mediators is one the advantages that this type of sensor offers because the mediators are leachable from the polymer network and are toxic.

Nano-structured materials used for developing novel sensors have been reported in the last decade. Colloidal nano gold particles have been extensively studied for the utility of promoting DET between enzymes and the nano particles (see references 9-10). Joseph Wang had extensive review articles in this field (see references 11-12). The carbon nanotube modified glucose oxidase (GOD) enzyme electrode capable of promoting electron transfer is reviewed in his articles. Vaseashta and Irudayaraj have a review paper on nanostructured sensors (see reference 13).

Nanowire and nanopore based sensors have drawn great interest recently because they are extremely sensitive and well suited for multiple target detection, which overcame the disadvantages of previous technology. However, as the reviewers Vaseashta and Irudayaraj point out, the technology is still in the development stage and the robustness has not been established (see reference 13). It has been shown that the nanopores played an important role in enabling multiple step reactions with higher reaction rate in comparison with the same system immobilized on polystyrene without nanopores (see reference 14).

Cylcodextrins (CD) existing in nature consists of 6 to 12 glucose units. The shapes of cyclodextrins are like donuts, or a truncated conical basket. These CDs have an internal hydrophobic property and external hydrophilic property. The internal pore diameter is 0.78 nm for $\beta$-CD, and its height is 0.78 nm. In the reports on recent development in this field, biosensors were developed utilizing the unique properties of CDs to form nanopores or nanotubes with polymers and biological materials (see references 17-22) to detect various toxic substances which are undetectable by conventional sensors.

As indicated above, however, robust nanopore structured sensors have yet to be reported. Therefore, there is a need for a biosensor for accurate glucose measurement, especially in the hypoglycemia range. In addition, there is a need for biosensors that do not utilize a mediator. These and other needs have been met by the present invention.

[Following are the CIP Application Background]

Demanding on a medical diagnostic device has multiple analytes detection and monitoring capabilities with less power consumption has been increased in recent years. Especially for most implantable medical devices, they need battery power up, however, higher power consumption means shorter lifetime of the device. For a remotely powered device, higher power consumption will decrease its communication distance. Moreover, more heat will be generated due to higher power consumption from the implant which may damage the contact tissue. Implantable biosensors are facing design challenges of signal drafting, corrosion; frequent calibration and instability due to body fluid interference (reference 1-5). For example, the implantable glucose biosensors used for continuous monitoring glucose for type 1 diabetes and for monitoring glucose in trauma brain injured (TBI) tissue, are prone to above mentioned drawbacks.

Each year cancer claims the lives of millions. The conventional methods for detection of low abundant cancer biomarkers are both time consuming and costly. The current methodologies are impractical with respect to a global health setting. Current imaging technologies are not capable of quantitative detection of the early stage cancers. Although transducer technologies such as optical and electrochemical have made great progress, direct screening of cancer cells relies on enzymatic reactions, such as alkaline phasphatase (ALP) interacting with p-amino alkaline phosphate (APP) substrates on an electrochemical sensor [Reference 6]. This technique depends on biopsy samples, which is invasive and inaccurate; the enzymatic reactions are subject to interference. The more traditional antibody immunosensor technology is both time consuming and costly. We propose to develop an enzyme-free and reagent-free cancer screening sensor based on a newly developed bio-inspired membrane with transmembrane receptors, such as fibroblast growth factor receptor 1 (FGFR1) [Reference 7] to be able to screening multiple analytes, such as breast cancer, pancreatic cancer, salivary gland adenosarcomas, Kaposi's sarcomas, ovarian cancers, prostate cancers and colon cancers, because enhanced protein tyrosine kinase (PTK) activity due to activating mutations of over expression has been implicated in these cancers [Reference 7-8].

SUMMARY OF THE INVENTION

It is an object of the present invention to provide a sensor comprising an electrode and a cyclodextrin in the form of a nanopore and chemically modified to be electrocatalytically active affixed to said electrode. The nanopore structured self-assembling membrane (SAM) sensors can be used for direct measurement of analyte without using the polymer network's leachable and potentially toxic mediators.

It is also an object of the present invention to provide a new generation of electrochemical glucose biosensor that is based on a nanopore structured cyclodextrin SAM and a biomimetic histidine residue (His 516) receptor of glucose oxidase that is located inside of the CD cavity. The biosensor of the present invention has demonstrated robust analytical performance for direct glucose measurements, especially in the hypoglycemia range.

It is a further object of the present invention to provide a method for detecting or measuring a material, such as glucose, in a sample comprising the step of contacting the sample with a biosensor wherein the biosensor comprises a nanopore structured and chemically modified cyclodextrin.

It is a still further object of the present invention to provide a method for constructing a biosensor comprising the step of contacting an electrode with a solution comprising chemically modified cyclodextrin to form a nanopore structure. In preferred embodiments, the cyclodextrin may be mM-β-DMCD (mono-modified β-dimethylcyclodextrin) and it forms self-assembling membrane together with PEG (polyethylene glycol) and PVP (poly(4-vinylpyridine)).

It is an object of the Continuation in Part (CIP) invention to provide an multiple channeling arrayed sensor comprising multiple electrodes and a cyclodextrin in the form of a nanopore and chemically modified to be electrocatalytically active vertically affixed to said electrode. The nanopore structured self-assembling membrane (SAM) sensors can be used for direct measurement of multiple analytes without using the polymer network's leachable and potentially toxic mediators or nature enzymes.

It is also an object of the Continuation in Part (CIP) invention to provide a new generation of electrochemical multiple channeling arrayed multiple analytes biosensors that are based on arrayed nanopore structured cyclodextrin SAM and a biomimetic glucose oxidase that is located inside of the CD cavity. The biosensor of the present invention has demonstrated robust bioanalytical performance for direct multiple analytes measurements, such as glucose and cancer cells without pretreatment of sample, or filtering, especially for reagent-less and enzyme-free.

It is also an object of the Continuation in Part (CIP) invention to provide a new generation of electrochemical multiple channeling arrayed multiple analytes detecting biosensors that are based on arrayed nanopore structured cyclodextrin SAM and a biomimetic protein tyrosine kinase (PTK) domain of Fibroblast growth factor receptor 1 (FGFR1) with the enhanced activity, that is located inside of the CD cavity. The biosensor of the present invention has demonstrated robust bioanalytical performance for direct multiple analytes measurements, such as a wide concentration range for glucose and a single cancer cell detection without pretreatment of the sample, or filtering the sample, especially under reagent-less and nature enzyme-free conditions.

It is still a further object of the Continuation in Part (CIP) invention to provide electrochemical multiple channeling arrayed multiple analytes detecting biosensors that are based on arrayed nanopore structured cyclodextrin SAM and a biomimetic protein tyrosine kinase (PTK) domain of Fibroblast growth factor receptor 1 (FGFR1) with the enhanced activity, that the single cancer cell is fixed into the position requirement of the 3D conformation without leaking out of the polymer membrane network. This current invention has demonstrated robust bioanalytical performance.

It is a further object of the present invention to provide a method for detecting or measuring a material, such as glucose, in a sample comprising the step of contacting the sample with a biosensor wherein the biosensor comprises a nanopore structured and chemically modified cyclodextrin.

It is a still further object of the present invention to provide a method for constructing a biosensor comprising the step of contacting an electrode with a solution comprising chemically modified cyclodextrin to form a nanopore structure. In preferred embodiments, the cyclodextrin may be mM-β-DMCD (mono-modified β-dimethylcyclodextrin) and it forms self-assembling membrane together with PEG (polyethylene glycol) and PVP (poly(4-vinylpyridine)).

It is a further object of the present invention to provide a method for detecting or measuring a material, such as cancer cell in a sample comprising the step of contacting the sample with a biosensor wherein the biosensor comprises a nanopore structured and chemically modified cyclodextrin.

It is a still further object of the present invention to provide a method for constructing a biosensor comprising the step of contacting an electrode with a solution comprising chemically modified cyclodextrin to form a nanopore structure. In preferred embodiments, the cyclodextrin may be triacetyl-β-cyclodextrin (T-CD), and it forms self-assembling membrane together with PEG (polyethylene glycol) and β-CD co-polymer.

BRIEF DESCRIPTION OF THE DRAWINGS

FIG. 1A shows two-dimensional atomic force microscopy (AFM) image of nanopore structured mM-β-DMCD/PEG/PVP SAM with an internal receptor imidazolyle. Brighter areas represent higher topography. The roughness measurements Peak-to-Valley (Z range), Root Mean Square (RMS), and Average Roughness ($R_a$) are also shown for this image.

FIG. 1D illustrates that mM-β-DMCD/PEG/PVP with nanopore structure forms conductive polymer blocks.

FIGS. 2A and 2B show AFM 3D images of mM-β-DMCD/PEG without nanopore structure, respectively.

FIG. 2C illustrates mM-β-DMCD/PEG with nanopillar structure.

FIGS. 3A and 3B show AFM images of TCD/PEG/PVP CD copolymer gold electrode without nanopore structure, respectively.

FIG. 3C illustrates T-β-CD/PEG/PVP cross-linking CD copolymer.

FIG. 4A shows the current vs. voltage Cyclic Voltammetry (CV) curves of a: the mM-β-DMCD/PEG/PVP SAM electrode with nanopore in 0.1M pH 7.0 buffer; b: the same sensor in the presence of 50 mg/dL glucose at scan rate 50 mv/s.

FIG. 4B shows CV curves of a: bare gold electrode without glucose, b: the T-β-CD/PEG/PVP CD copolymer electrode without glucose in the 0.1M pH 7.0 buffer under same experimental conditions.

FIG. 4C shows CV curves of a: mM-β-DMCD/PEG SAM electrode without glucose, b: with 50 mg/dL glucose.

FIG. 5 shows CV profiles for the nanopored sensor with the mM-β-DMCD/PEG/PVP SAM membrane upon pH changes from 5.0 to 9.0 at same 0.1 M phosphate buffer with 0.1M KCl.

FIG. 6 shows the plots of normalized CV profiles of the same sensor as in FIG. 5 in the presence of various glucose concentrations from 5 mg/dL increased to 250 mg/dL labeled a to g, respectively.

FIG. 7 shows the plot of current vs. glucose concentration by using a sensor in FIG. 6.

FIG. 11 is a representation of the structure of a catalytically active cyclodextrin.

FIG. 15A illustrates the effect of inhibitor o-NPA on the sensor Au/TCD/PEG/Co-polymer performance using double chronopotentiometry method in the presence of 5, 50 and 100 living breast cancer cells/mL with 13 mM o-NPA from line (a to d) at ±10 mA without incubation against a negative control culture solution with o-NPA as the dotted line; Compared with line (e) 5 cell/mL without inhibitor o-NPA under the same experimental conditions.

FIG. 20 illustrates the chronoamperometric profiles of sensor Au/MCD/PEG/PVP with or without breast cancer cells after 24 hrs incubation in cultural media (a) control, 0 cell; (b) 1 cell/mL; (c) 5 cell/mL; (d) 50 cell/mL; (e) 100 cell/mL under appE1 −200 mV and appE2 −400 mV with step 60 ms.

FIG. 22-b Illustrates a top-down, two-dimensional view of the individual component parts of the v-shaped sensor.

FIG. 22-c Illustrates a top-down, two-dimensional view of the individual pieces that comprise the v-shaped sensor.

FIG. 24-b Illustrates a front-facing close-up view of the circuitry etched on each individual electrode.

FIG. 24-c Illustrates an isometric 3-d view of the prototype redesign.

DETAILED DESCRIPTION OF THE INVENTION

Example 1

Constructing the Biosensor

Figure 1B:
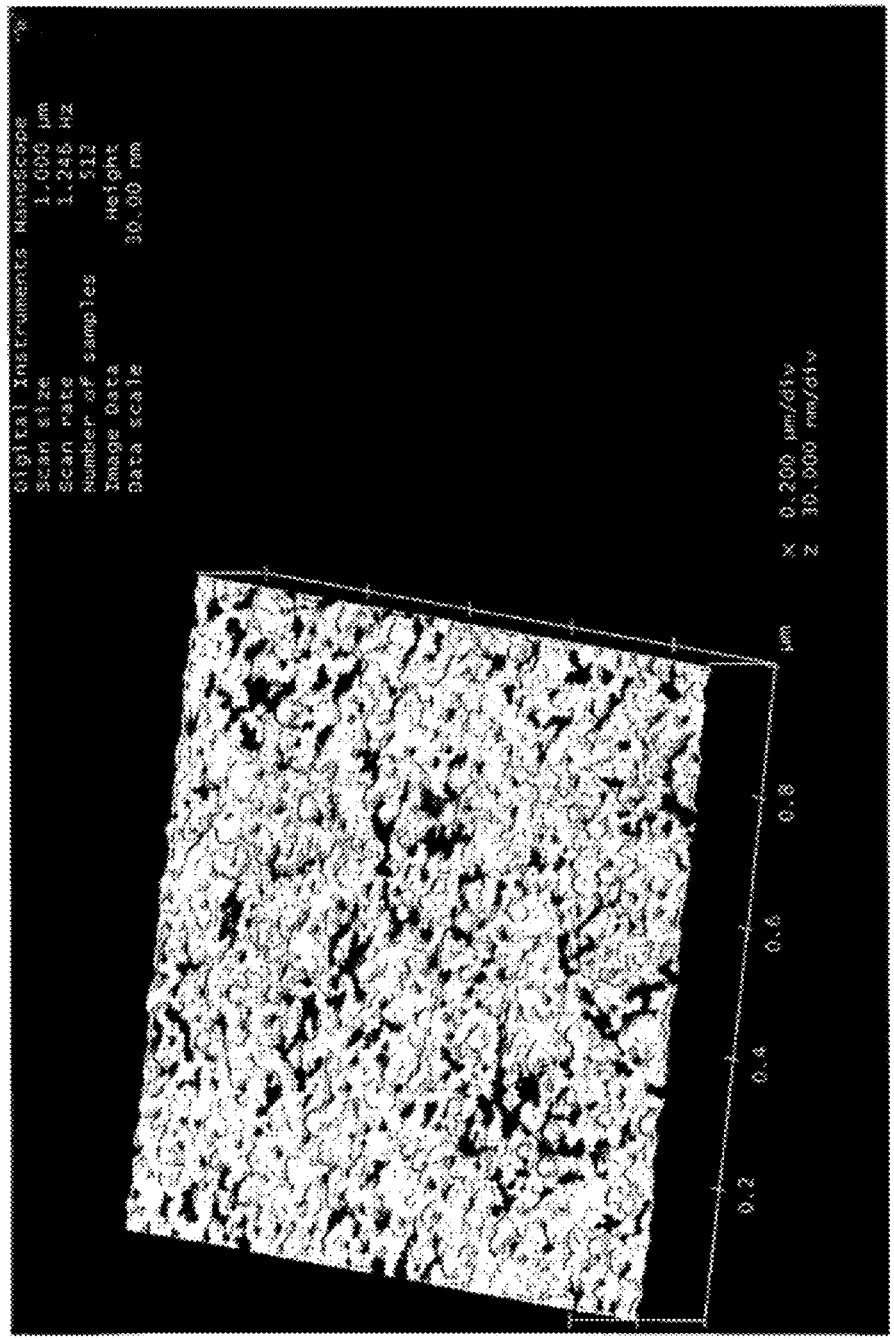
FIGS. 1B and 1C show 3D AFM (Atomic Force Microscopy) images for the same sensor as in FIG. 1A, respectively.

Reagent grade poly (4-vinylpyridine) (PVP), polyethylene glycol diglycidyl ether (PEG), triacetyl-β-CD (T-β-CD), β-CD/epichlorohydrin, β-D-glucose were purchased from Aldrich-Sigma. The PVP was recrystallized in methanol. The biomimetic glucose enzyme, which is a biomimetic Histidine residue (His-516) receptor of glucose oxidase and mimics the active center of native glucose enzyme, named mM-β-DMCD was synthesized generally according to the published procedures (E. T. Chen and H. L. Pardue, *Analytical applications of catalytic properties of modified-cyclodextrins*. Anal. Chem. 65, 2563-2567, 1993, which is hereby incorporated by reference in its entirety as if set forth herein). U.S. Pat. No. 6,582,583 issued on Jun. 24, 2003 is also hereby incorporated by reference in its entirety as if set forth herein. Briefly, β-DMCD may be reacted first with sodium hydride in dry tetrahydrofuran under a nitrogen atmosphere at 35-38° C. for 10 hours. The solution is then cooled to 0° C. and mixed with a solution of 2-(4-imidazolyl)-ethyl bromide in tetrahydrofuran and heated to 25° C. for 10 hours to produce the mM-β-DMCD. The structure of the mM-β-DMCD is shown in FIG. 11.

A gold electrode (1.6 mm diameter) polished successively with 0.1 and 0.05 µm alumina slurry (BAS), then washed with double distillation water, then sonicated with methanol, then with water. After that, the electrode was polished with diamond solution (BAS), and washed with double distillation water and sonicated in methanol, then with double distillation water. Dry $N_2$ was used to dry the electrode, and then the gold electrode was put in a 35° C. incubator for further drying for 1 hour before use. The gold electrode with a SAM film was used as the working electrode. The platinum wire electrode was the auxiliary electrode and the Ag/AgCl electrode was the reference electrode.

A class 100 level of a clean room was used for all SAM developments. A mixture of PVP/PEG/mM-β-DMCD (see E. T. Chen. *Amperometric biomimetic enzyme sensors based on modified cyclodextrin as electrocatalysts*, and U.S. Pat. No. 6,582,583 issued on Jun. 24, 2003, both of which are hereby incorporated by reference in entirety as if set forth herein) solution (e.g. 4 μL) was dropped using a syringe by 2×4 μL onto the gold electrode surface at a room temperature and the fabricated SAM electrode was immediately sealed in a $N_2$ filled container and incubated for 48 hours at 35.0° C., then the electrode was washed with double distilled water to remove unbounded chemicals, then was incubated for 2 hours before use. The same protocols were used for fabrication of the PEG/mM-β-DMCD SAM film without PVP; and a T-β-CD/PEG/PVP/β-CD copolymer SAM sensor was also fabricated under the same procedures. The differences in the composition and concentration between the U.S. Pat. No. 6,582,583 and an embodiment of the present invention is shown below:

TABLE 1

Comparison of the composition and concentration of the PVP/PEG/mM-β-DMCD mixture

| | Composition (v/v) | | | Concentration (mg/mL) | | |
| --- | --- | --- | --- | --- | --- | --- |
| | PVP: | PEG: | mM-β-DMCD | PVP: | PEG: | mM-β-DMCD |
| U.S. Pat. No. 6,582,583 | 5 | 2 | 10 | 4 | 2 | 4.0 |
| The embodiment of the present invention | 3 | 1 | 6 | 0.4 | 2 | 4.2 |

It should be noted that different factors have impacts on the formation of different nanostructured SAM film on a gold surface. A comparison of these factors in an embodiment of the present invention and U.S. Pat. No. 6,582,583 is shown below:

TABLE 2

Comparison of the structure of the gold film

| | the gold film | Film thickness |
| --- | --- | --- |
| U.S. Pat. No. 6,582,583 | Single crystal AU(1,1,1) | 10 nm |
| The embodiment of the present invention | The purity >99.99% | 50 nm |

A single crystal gold 1×1×1 film that causes phase structure transition was reported in Y. Kondo et al. (see reference 28). The different thickness of the gold film has an impact on the formation of the SAM film on the gold surface.

TABLE 3

Comparison of the processing procedure

| | Cleaning procedure on the gold surface | Fabrication procedure |
| --- | --- | --- |
| U.S. Pat. No. 6,582,583 | Ultra sonic plasma cleaning procedure was used. | To form the nanotube in FIG. 4 of the U.S. Pat. No. 6,582,583, the gold planer electrode was completely immersed into a solution consisting of PVP/PEG/mM-β-DMCD(5:2:10 (v/v)) in a sealed container for 24 hours at a room temperature, then the gold electrode was taken out and incubated for 48 hours at 37° C. and cleaned with distilled water for 10 minutes, then dried for 2 hours at 37° C. to allow the formation of the nanotube by self-assembly. |
| The embodiment of the present invention | No cleaning procedure was applied onto the gold surface. | To form the nanopore structure shown in FIGS. 1A, 1B and 1C, a drop (4 μL) of solution consisting of PVP/PEG/mM-β-DMCD was applied onto the gold chip surface at a room temperature and immediately incubated for 48 hours at 35° C. Then the gold electrode was taken out, cleaned with distilled water for 10 minuets and dried at 35° C. for 2 hours to allow the formation of the nanopore by self-assembly. |

In addition, according to U.S. Pat. No. 6,582,583, the gold planer electrode was immersed in the solution for 24 hours at a room temperature. However, in an embodiment of the present invention, only one drop of the solution was applied onto the gold chip surface. After the application, the solution was immediately taken into incubation. The step of immersion in a sealed temperature for 24 hours at a room temperature was skipped.

Example 2

AFM Measurements

A clean bare gold chip with 50 nm thickness and 3 mm diameter was purchased (GeneFluidics, Calif.) for fabrication of the CD-SAM. Pretreatment of the chip before the fabrication is not necessary based on the AFM image of the bare gold surface. The same procedures and chemical mixtures as above were used to fabricate the gold CD-SAM chip in the clean room for the AFM measurements. The morphology of the three CD-SAMs against a bare gold electrode was characterized by using an instrument (Digital Instruments Dimension 3100 Atomic Force Microscope, Veeco Instruments, Santa Barbara, Calif.). The nanopore sizes were measured using TappingMode™ AFM with a silicon cantilever and tip with a 300 kHz resonance frequency and a 5-10 nm tip radius (Model TESP by VeecoProbes). The software used was NanoScope versions 5.30r1.

Figure 1C:
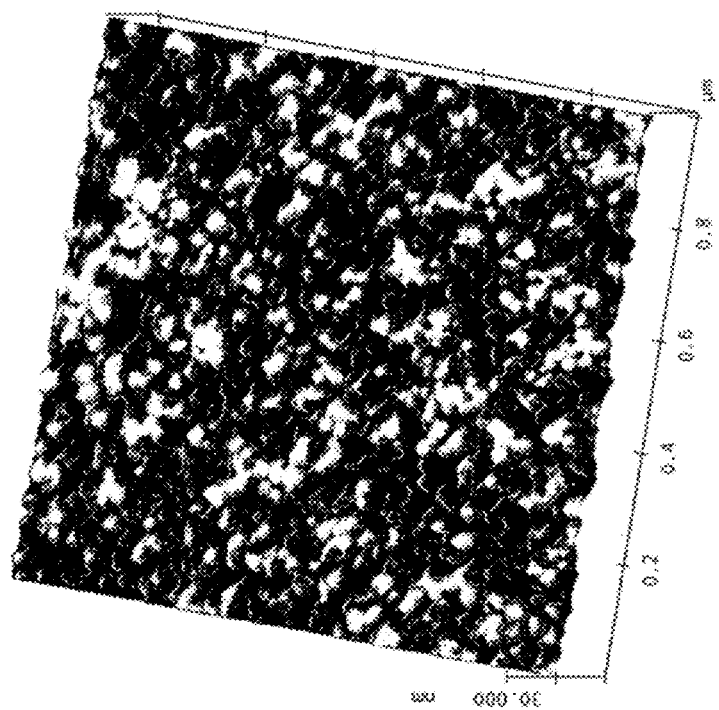
Figure 1E:
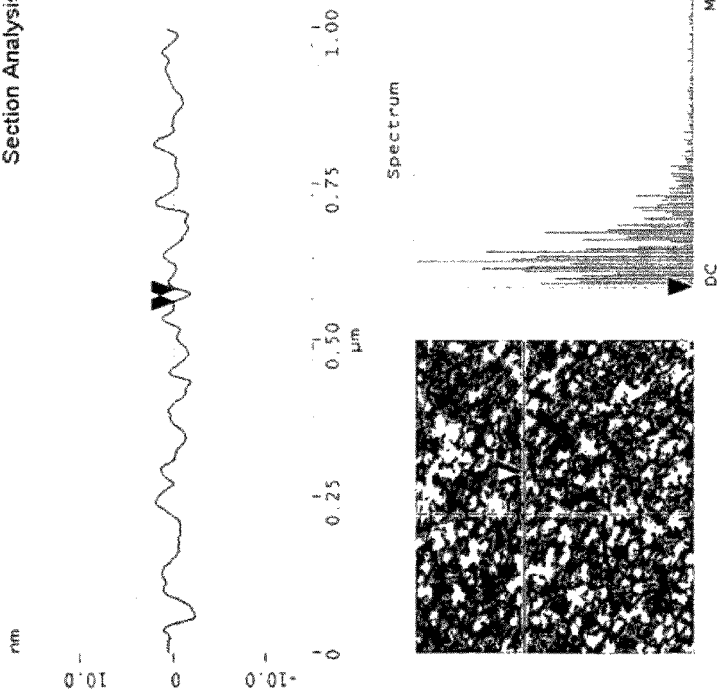
FIG. 1E shows the cross-sectional nanopore size measurement of the same sensor as in FIG. 1A.

The first reported nanopore structured biomimetic CD-SAM was shown in FIG. 1A (two dimensional view, roughness measurement), FIGS. 1B and 1C (3D view), FIG. 1D (illustrative drawing) and FIG. 1E (pore size measurement).

Figure 2A:
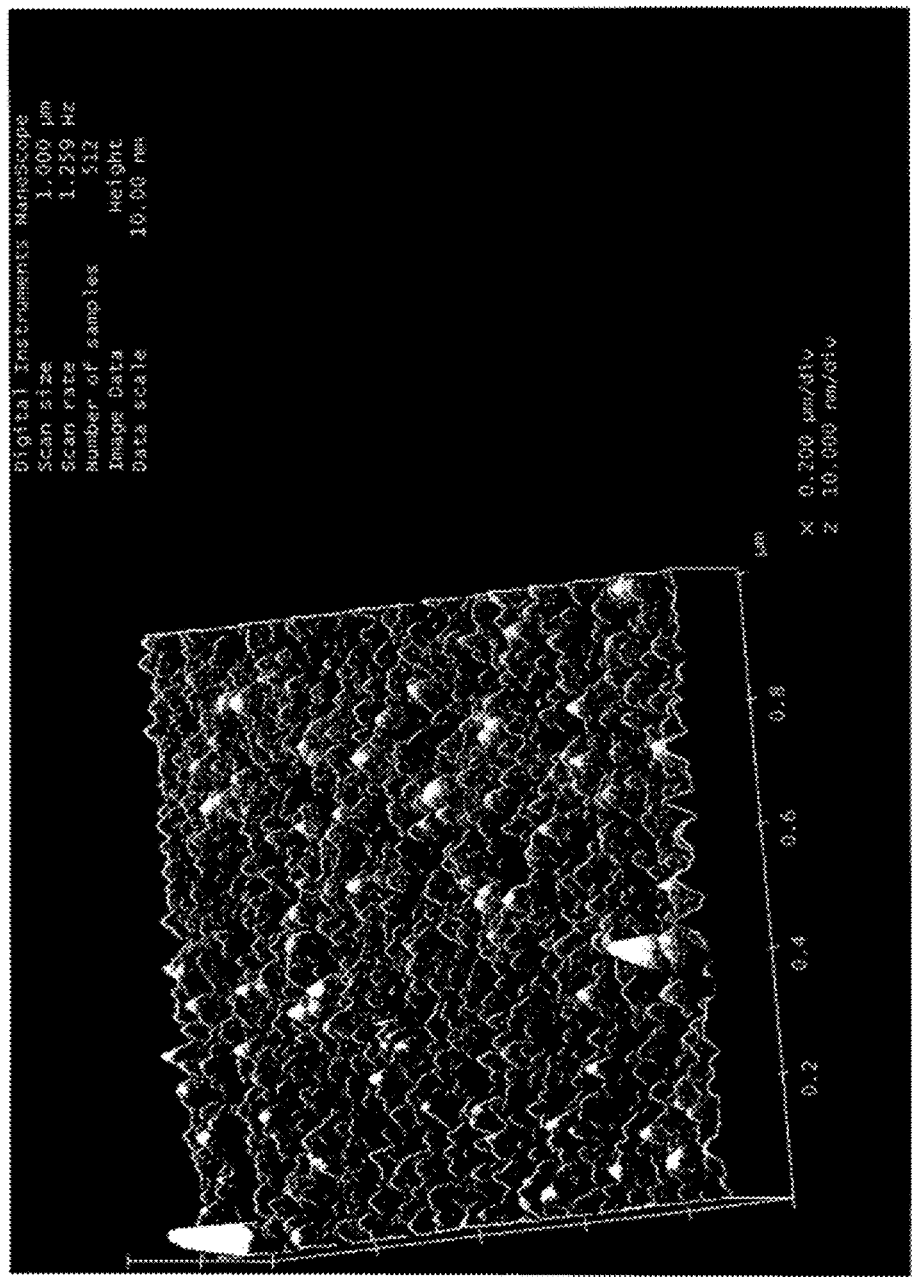

The images clearly revealed the smoothness of the SAM and the fact that the nanopores were evenly distributed and vertically oriented on the gold surface with the pore size from 10 nm to 20 nm, and the roughness of the SAM was 0.82 nm RMS. FIGS. 1D and 1E show the example of the pore size of 19.5 nm. FIGS. 2A and 2B are the 3D AFM images for a sensor with the same chemical composition and the receptor, but without nanopore structure. The nanopores were not observed. However, a "forest" of nano pillars (10-60 nm diameter) was observed covering the gold surface with a relative roughness of 16.65 nm in the z direction of the membrane, which was much rougher than the former sensor. FIGS. 3A and 3B are the AFM images for another type of sensors that were fabricated by the inventor, which had the same configuration as the sensor in FIG. 1A, except that triacetyl-β-CD(T-β-CD) instead of the receptored CD was used. The relative film roughness of the SAM membrane was 24.6 nm, which was too rough and the signature nanopore structure was not observed.

Example 3

Electrochemical Measurements

A voltammetric analyzer (model CV50W, Bioanalytical System (BAS), IN) was used for the measurements of currents. A Faraday low current cage (model C2, BAS) was used for protection of the electrode cell. For the pH effect study and for the glucose measurements, the scan rate was kept constant at 50 mv/s. All electrochemical measurements were done in an unstirred electrochemical cell at 20° C. All sample solutions were bubbled thoroughly with high purity $N_2$ for 10 minutes and maintained in a $N_2$ blanket. The 0.1 M, pH 7.0±0.1 buffer ((0.1 M KCl) solution was filtrated and degassed. The electrodes were equilibrated in a 10 mL, pH 7.0±0.1, 0.1 M buffer (0.1 M KCl) for 30-45 minutes by applying a potential at −400 mv until a steady-state current was observed before a sample can be measured.

The internal standard addition method was used to study the accuracy of glucose measurements using bovine serum albumin (BSA). The current for a 50 mg/dL glucose standard was measured in the 0.1M phosphate buffer, pH 7 (0.1M KCl) bovine serum albumin. Then 100 μL of 5 g/dL of glucose solution was added into the sera, and the current was measured. Four measurements were obtained after 4 consecutively additions of the same amount of glucose solution.

The electrochemical behavior of the sensors was characterized by using Cylic Voltammetry (CV) method. The factors affecting the currents were studied. The cyclic voltammograms of different electrodes with and without nanopore structured SAM membranes are compared in FIGS. 4A, 4B and 4C. In FIG. 4A, a well-defined irreversible reduction peak was observed for the nanopore sensor curves a and b, indicating that the nanopore structured CD-SAM was favorable for the DET between the active center of the imidazolyl in the cavity of mM-β-DMCD and the electrode. The decrease of the current shown in curve b indicates that the glucose molecules entered the CD cavity and mingled with the active receptor, hence suppressing the DET between the receptor and the electrode. FIG. 4B shows the electrochemical behavior for the T-β-CD's SAM electrode. The curves a and b have large envelop background currents. No DET peaks were observed for the bare gold electrode and for the T-β-CD electrode. FIG. 4C shows that there is no DET peak for mM-β-DMCD without nanopore structure, even it has the mimic His receptor, in the presence or absence of glucose. In FIG. 4C, the curves a and b overlap and the heavy envelop-like background currents exist, which was consistent with the morphology of the AFM image. FIG. 4A shows the electrocatalytic current and FIG. 4C does not have the current, even both sensors had the same biomimetic receptor, the differences being that the biosensor in FIG. 4A has the nanopore structure and the biosensor in FIG. 4C does not have the nanopore structure. This indicates that a lack of nanopore structure could hamper the DET even in the presence of an active receptor.

Example 4

Scan Rate Effects

Figure 9:
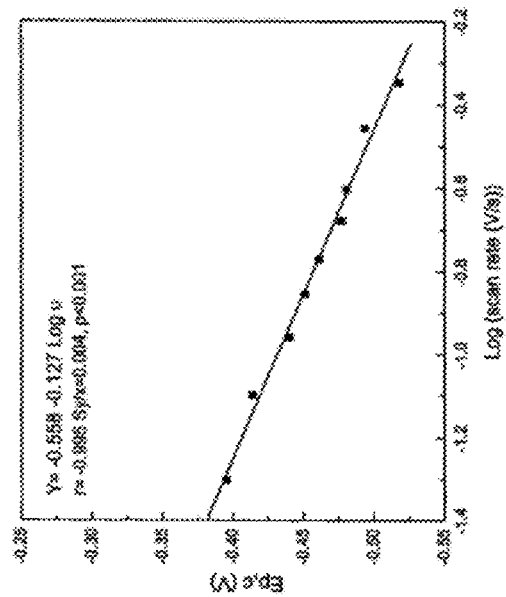
FIG. 9 shows the plot of $E_{p,c}$ (V) potential vs. long (υ) scan rate according to the current obtained from the CV profiles in FIG. 8.
Figure 8:
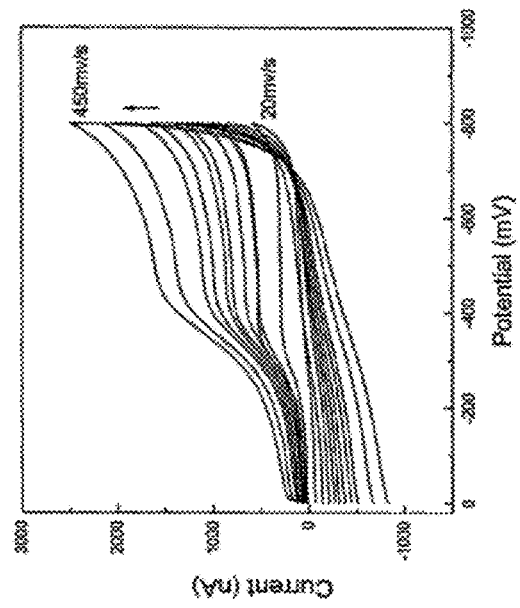
FIG. 8 shows the CV current profiles against the changing of scan rate at 20.0° C., pH 7.0±0.1, 0.1 M phosphate buffer (0.1 M KCl). The scan rate changed from 20 to 450 mv/s.

The scan rate effects on the electrochemical behavior of the nanopore CD sensor were studied and the voltammogram profiles were shown in FIG. 8. The reduction peak currents increased as the scan rate increased in the studied range from 20 mv/s up to 450 mv/s. The linearity study of the scan rate effect on the $E_{p,c}$ values is presented in FIG. 9. The nanopore structured CD sensor distinguished itself from other reported sensors that had reversible redox peaks (see references 3, 9, 25) and associated with the DET effect, which was the irreversible direct electron transfer. Possible explanations were that the effects of the nanopore structures were significant on DET. It played a significant role in promoting the DET. According to the commonly used E. Laviron's method, the DET rate constant for one nanopore structured CD-SAM sensor was calculated as 131±2.3/s based on three replicate measurements in neutral buffer, which had a 3.4-fold increased DET compared with 38.9±5.3/s for the rate constant for a gold nanoparticle-based glucose sensor using native glucose enzymes (see reference 9). The results also had a 3.11-fold faster rate than a GOD glucose sensor with single-walled carbon nanotubes (see reference 12).

Some of the advantages of the nanopored CD sensors of the present invention over the prior art native glucose enzyme sensors with gold nanoparticles or carbon nanotubes are: (1) the activation of the biosensor without the need of the presence of oxygen to detect glucose simplifies the procedures for commercialization; (2) the fabrication of truly reagentless, mediatorless nanopore CD sensors without the use of glucose enzyme avoided biofouling and denaturing from using native enzymes, which is an attractive characteristic for implantable devices or for usage in harmful environments.

Example 5 pH Effects

The change of pH effects on the electrochemical behavior of the nanopored CD sensors was evaluated in 0.1 M phosphate buffer with varied pH from 5.0 to 9.0 without the presence of glucose at 20° C. as shown in FIG. 5. The highest peak intensity was observed at pH 7.0. The cathodic peak diminished at pH 9.0 indicated more negative ions from the solvent solution suppress the DET electron flow. The peak shifting slightly to a positive potential due to a decrease of pH was also observed. Therefore, the sensor is useful over a pH range of from about 5.0 to about 8.0.

Example 6

Nanopore Channeling Effect

Under optimal experimental conditions, curve c in FIG. 5 shows the optimal results, where DET occurred at a reduced potential around −390 mV. The cyclic voltammogram profiles are shown in FIG. 6 upon the addition of various standard glucose concentrations successively in the 10 mL pH 7.2 buffer solution. As shown in FIG. 4A, for curve b, the current decreases in the presence of glucose. The fact that electro-catalytic current increased proportionally with higher glucose concentration indicates that the channeling effect due to the nanopore structure had overcome the effect of glucose-receptor reaction resulting in the temporary suppression of the direct electron transfer. Recent published literature has revealed the fact that a decrease in current was observed as analyte concentration increased in gold nanoparticle sensors when native enzymes were used (see references 3, 9). This further provided evidence proving that when β-CD is lodged in the lumen of the α-hemolysin (HL) pore, it reduces the unitary conductance by about 70% (see reference 16), and the current reduces significantly when a voltage is applied onto the biological system in comparison with a system without an β-CD entering the α-HL pore.

Figure 10:
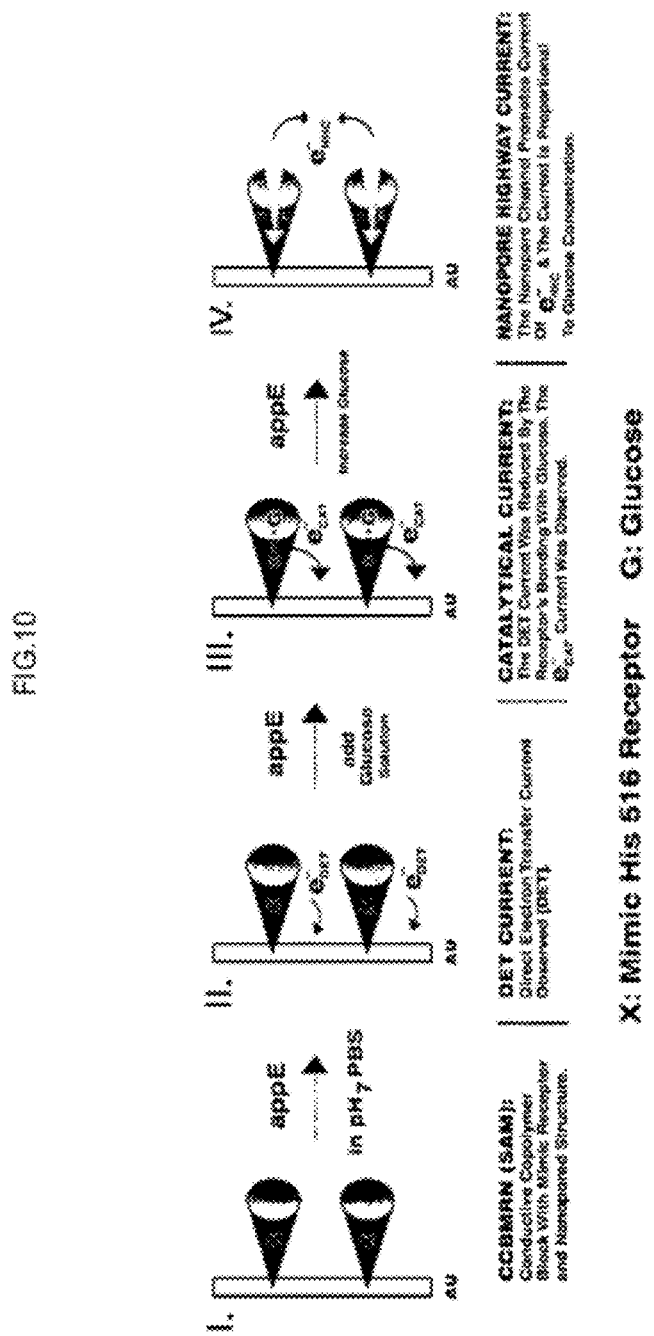
FIG. 10 illustrates the pathway for a nanopore sensor under an applied potential.

The experiments of the present invention not only confirm the nanopore sensor's electrochemical function, but also reveal a distinct phenomenon: at the beginning, a decrease of current is due to the association of the glucose molecules with the receptor site, and after that, an proportional increase of current is due to the nanopore channeling effect when the glucose concentration continues to increase. Detailed illustration of the pathway of the nanopore sensor is presented in FIG. 10.

Example 7

Accuracy and Biosensor Durability

For within-run precision, the relative mean standard deviation (RSD) was 1.5% from the triplicate runs obtained at each of 11 glucose concentration levels from 5 to 100 mg/dL. At the clinical decision level of 50 mg/dL, the RSD values were 1.1% and 1.4% (n=5) obtained at different days using the same nanopored CD sensor #1. At 20 mg/dL, which is a useful clinical decision level for diagnosing type I diabetic in newborns (see reference 23), the RSD value was 1.5%. For the inter-assay precision, the RSD values obtained from three CD sensors #1 with the same nanopored fabrication were 1.1%, 0.7% and 2% at 50.0 mg/dL glucose concentration with five replicates. The precision measurements of glucose at hypoglycemia range from the nanopored CD sensors have laid a foundation for accurate performance for future glucose monitoring devices. This improvement of the analytical performance has overcome the disadvantage of imprecise measurements common to self-monitoring blood glucose (SMBG) devices of the prior art at the low glucose range (see reference 23).

Three same types of nanopore structured CD sensor were fabricated on three 1.6 mm diameter gold electrodes and were used for the reproducibility study. The DET rate constants can be reproducibly obtained. The $K_s$ value was 136.7/s±19/s. The peak intensity deviation among the three sensors was 7.7%.

The internal standard addition method was used to study the accuracy of glucose measurements using bovine serum albumin (see reference 26). Four measurements were obtained after 4 consecutively additions of the 100 μL of 5 g/dL of glucose solution into the BSA. The results were compared against an internal standard. The mean accuracy was 98%±1% at 50 mg/dL concentration.

In prior art, native glucose enzyme sensors can suffer biofouling in which the glucose enzyme is easily dissociated from the electrode surface (see reference 9), and, therefore, it needs constant enzyme activity renewal in a solution. This problem does not occur with the nanopored CD sensor of the present invention. The CD sensor of the present invention never needs such a renewal process and still maintains a good performance. For example, the intensity of the same CD sensor only decrease by 16% after 116 measurements lasted for 42 days. Plus, the sensor does not need to be kept at 4° C. for storage as required by native enzyme sensors (see reference 3). Therefore, the nanopore CD sensors of the present invention have offered advantageous features that are simple and robust for direct glucose measurements without using glucose enzymes or mediators.

Example 8

Sensitivity of an Arrayed-Nanopored Biosensor

As shown in FIG. 6, the well-defined electrocatalytic response curves for glucose are presented by utilizing the arrayed-nanopore SAM with an artificial electrocatalytical functioning receptor. A plot of current vs. glucose concentration illustrates the linearity of the nanopored CD sensor's analytical performance presented in FIG. 7. The least-squares statistical results obtained from current vs. glucose concentrations produced an equation Y(nA)=−0.9 (nA)+1.97×(nA/mgdL$^{-1}$) with a linear range up to 205 mg/dL with the Correlation Coefficient of r=0.998, $S_{y/x}$=10.7 nA. The sensitivity of the sensor is 3.55 nA/μmol/L in 2.01 mm$^2$ electrode surface, which is 118-fold sensitive than that of the prior arts (Chen, 2003, see reference 17), and 33,040-fold enhanced the sensitivity compared with Liu's glucose electrochemical cyclodextrin polymer sensor (Liu et al. 1998, see reference 27). The calculated Limit of Detection (LOD) for glucose using the current invented arrayed-nanopored sensor is 3.1 nM/mm$^2$, which are 1.9×10$^3$ molecules of glucose/nm$^2$.

Example 9

Performance at Hypoglycemia Range

This glucose biosensor of the present invention demonstrates the full usages of monitoring glucose at critical clinical decision concentration ranges (FIG. 7) from hypoglycemia to hyperglycemia ranges. The least-squares statistic result in the hypoglycemia range from 5 to 50 mg/dL produced an equation of y=−0.008 μA+0.007×(μA/mg/dL) with Correlation Coefficient of 0.999 (n=30 with three replicates at each of 10 concentration levels), and has the $S_{y/x}$ value of 0.006 μA, corresponding to a relative standard deviation of 1.6% at the 50 mg/dL clinical decision level for type I diabetic hypoglycemia.

Example 10

Glassy Carbon Electrode

In addition to gold, glassy carbon can be used for construction of the biosensor of the present invention. The DET effect was observed and the irreversible peaks were also obtained.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.
[Following Examples are for CIP Application]

Example 11

Constructing the Biosensor

Reagent grade poly(4-vinylpyridine) (PVP), polyethylene glycol diglycidyl ether (PEG), triacetyl-β-CD (T-β-CD) and β-CD/epichlorohydrin were purchased from Aldrich-Sigma. PVP was purified before use. The biomimetic glucose enzyme, which is a biomimetic Histidine residue (His-516) receptor of glucose oxidase and mimics the active center of native glucose enzyme, named mM-β-DMCD was synthesized generally according to the published procedures (E. T. Chen and H. L. Pardue, *Analytical applications of catalytic properties of modified-cyclodextrins*. Anal. Chem. 65, 2563-2567, 1993, which is hereby incorporated by reference in its entirety as if set forth herein). U.S. Pat. No. 6,582,583 issued on Jun. 24, 2003 is also hereby incorporated by reference in its entirety as if set forth herein. Briefly, β-DMCD may be reacted first with sodium hydride in dry tetrahydrofuran under a nitrogen atmosphere at 35-38° C. for 10 hours. The solution is then cooled to 0° C. and mixed with a solution of 2-(4-imidazolyl)-ethyl bromide in tetrahydrofuran and heated to 25° C. for 10 hours to produce the mM-β-DMCD. The structure of the mM-β-DMCD is shown in FIG. 11.

Each of the 16 sensor channel has a working electrode in the middle with 3 mm in diameter, and a reference gold electrode and an auxiliary gold electrode were separated by the working electrode. A class 100 level of a clean room was used for all SAM developments. A mixture of PVP/PEG/mM-β-DMCD (see E. T. Chen. *Amperometric biomimetic enzyme sensors based on modified cyclodextrin as electrocatalysts*, and U.S. Pat. No. 6,582,583 issued on Jun. 24, 2003, both of which are hereby incorporated by reference in entirety as if set forth herein) solution (e.g. 4 μL) was dropped using a pipette by 2×4 μL onto one of the channel gold electrode chip surface (50 nm thickness) (Genefluidics, Calif.) at a room temperature and the fabricated SAM electrode was immediately sealed in a $N_2$ filled container and incubated for 48 hours at 35.0° C., then the electrode was washed with double distilled water to remove unbounded chemicals, then was incubated for 2 hours before use. The same protocols were used for fabrication of the T-β-CD/PEG/β-CD copolymer SAM sensor was also fabricated under the same procedures. The differences in the composition and concentration between the U.S. Pat. No. 6,582,583 and an embodiment of the present invention is shown in Example 1.

Example 2

AFM Measurements

A clean bare gold chip with 50 nm thickness and 3 mm diameter was purchased (GeneFluidics, Calif.) for fabrication of the CD-SAM. Pretreatment of the chip before the fabrication is not necessary based on the AFM image of the bare gold surface. The same procedures and chemical mixtures as above were used to fabricate the gold CD-SAM chip in the clean room for the AFM measurements. The morphology of the three CD-SAMs against a bare gold electrode was characterized by using an instrument (Digital Instruments Dimension 3100 Atomic Force Microscope, Veeco Instruments, Santa Barbara, Calif.). The nanopore sizes were measured using TappingMode™ AFM with a silicon cantilever and tip with a 300 kHz resonance frequency and a 5-10 nm tip radius (Model TESP by VeecoProbes). The software used was NanoScope versions 5.30r1.

Figure 12A:
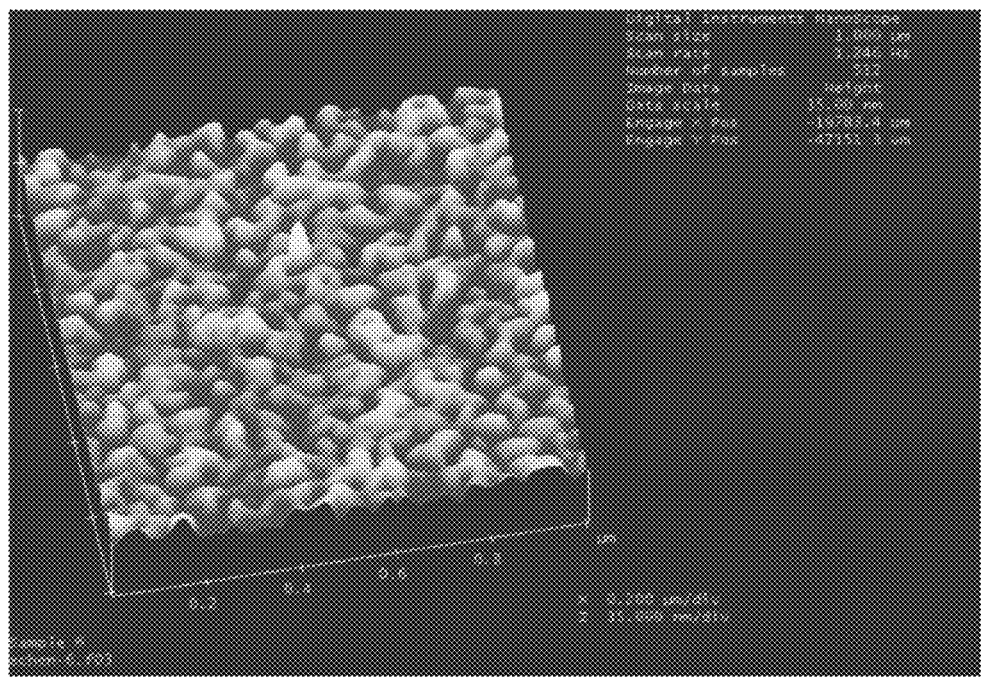
FIG. 12A illustrates the surface morphology of the Au/TCD/PEG/co-polymer self-assembling membrane using the Atomic Force Microscope (AFM) in a 3D view.
Figure 12B:
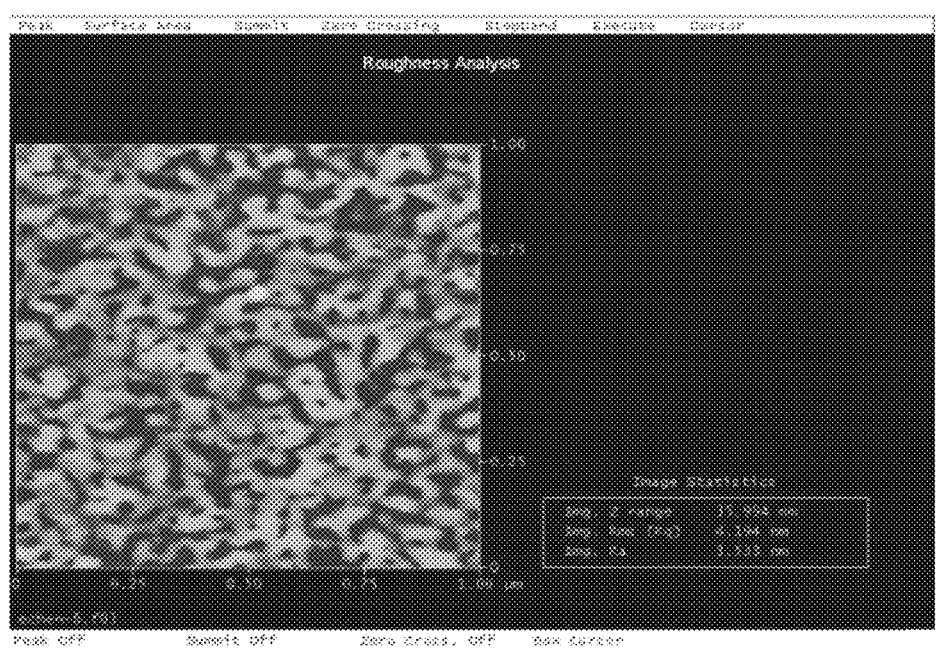
FIG. 12B Illustrates the 2D view of the Au/TCD/PEG/co-polymer self-assembling membrane using AFM.
Figure 12C:
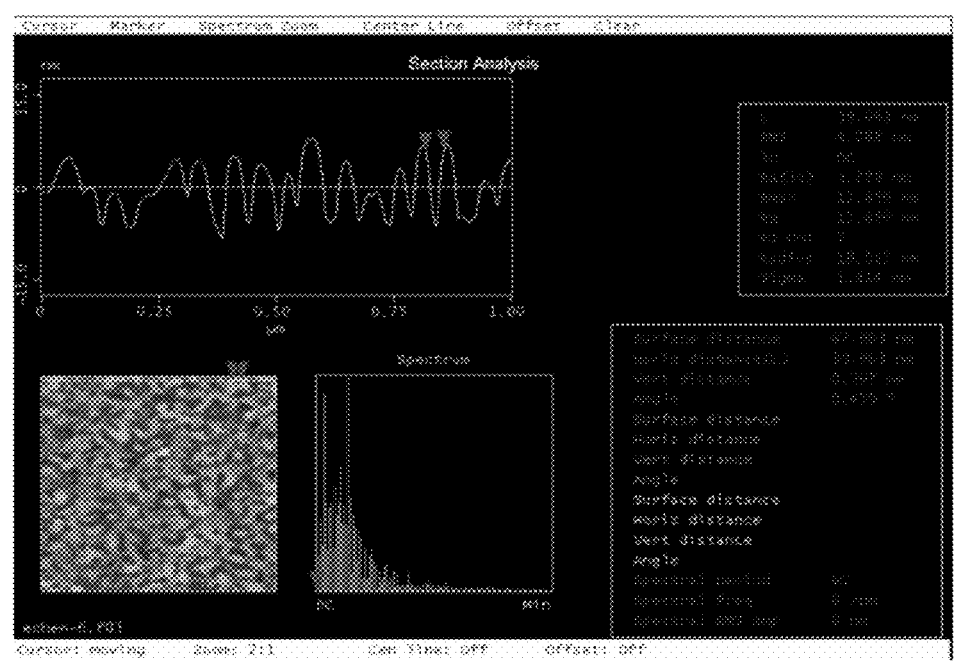
FIG. 12C characterizes the surface morphology of the Au/TCD/PEG/co-polymer self-assembling membrane by cross=section analysis with an average pore size about 40 nm with a RMS 4.2 nm.

The first reported nanopore structured biomimetic fibroblast growth factor receptor (FGFR) 1 CD-SAM on gold surface was shown in FIG. 12A (three dimensional view), FIG. 12B (2D view, roughness measurement), and FIG. 12C (cross-section analysis for pore size measurement and surface roughness measurement). The images clearly revealed the smoothness of the SAM and the fact that the nanopores were evenly distributed and vertically oriented on the gold surface with the pore size from 20 nm to 60 nm (in average of 40 nM), and the roughness of the SAM was 4.2 nm RMS. By only delete one component PVP, it has changed the entire landscape nanostructure, from FIGS. 3A and 3B's rough poreless structure to uniformly vertically oriented big pore 40 nm smooth structure with rms 4.2 nm. This change of structure and 3D conformational change has provided a crucial means for a better receptor-guest molecular complex or electron-relay, and the 40 nm pores enable even cancer cells to participate the electron-relay system.

Figure 13A:
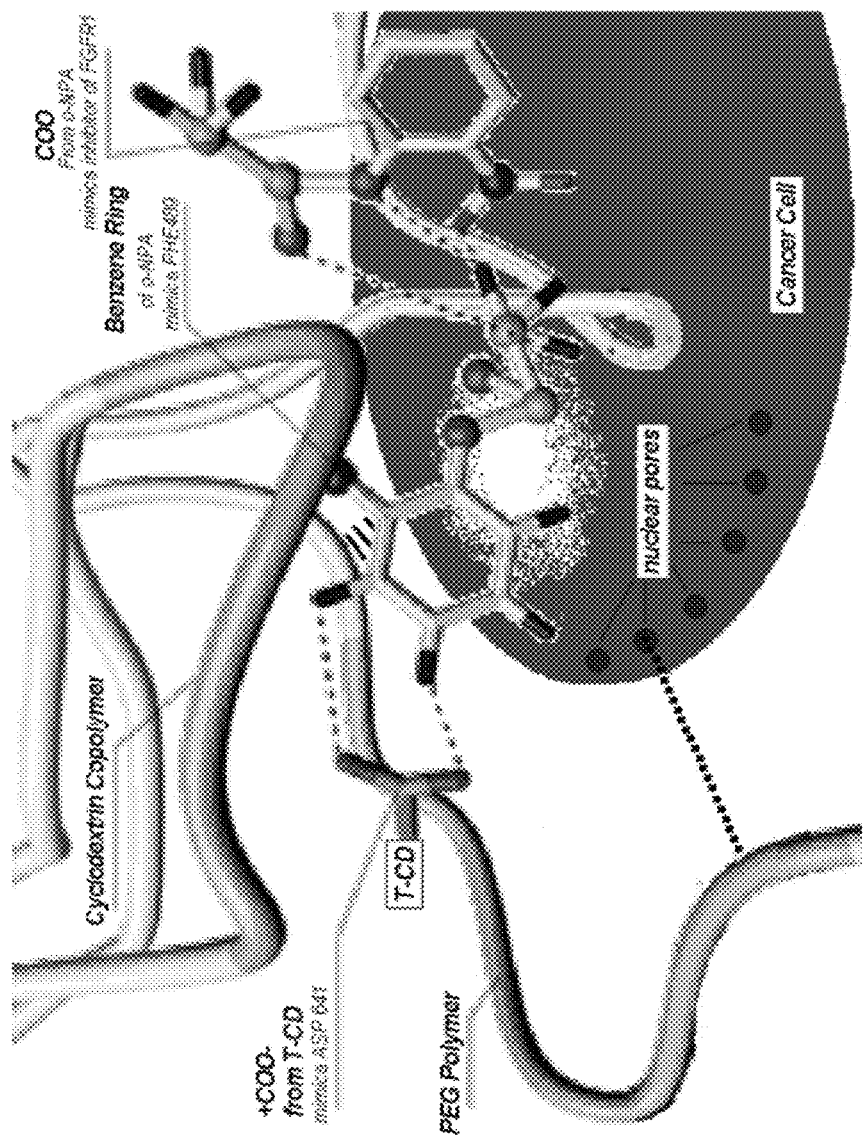
FIG. 13A illustrates the biomimetic electron-relay membrane using the structure of the Fibroblast Growth Factor (FGF) receptor 1-inhibitor complex model. O-NPA is the inhibitor.
Figure 13B:
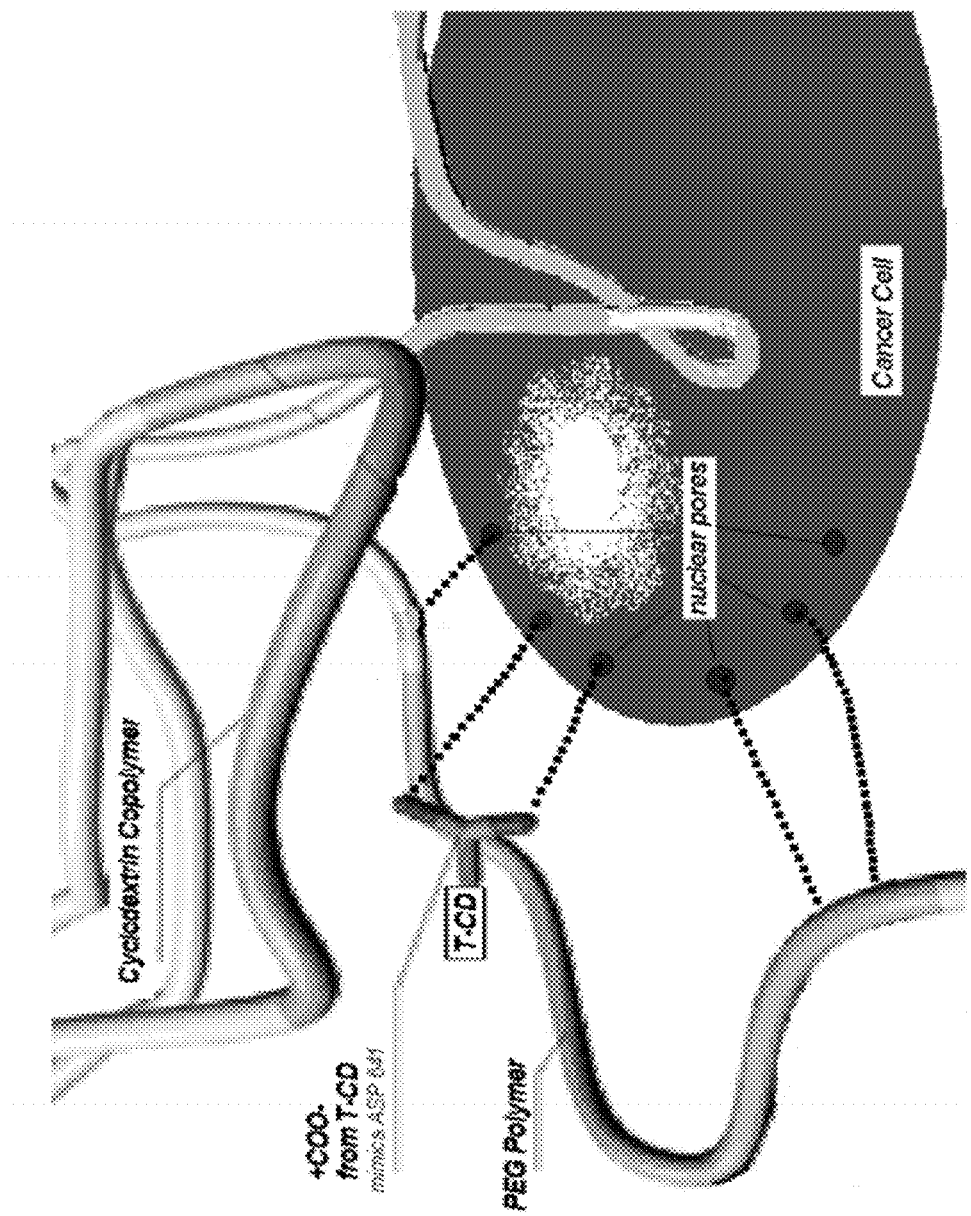
FIG. 13B illustrates the biomimetic electron-relay membrane using the structure of the Fibroblast Growth Factor (FGF) receptor 1-cancer cell complex model without an inhibitor.

FIG. 13A illustrate an art drawing of the inhibitor o-NPA enters the receptor active sites and formed electron-relay system with receptors and it effectively blocked the interaction between the cancer cell and the receptor of FGFR1. FIG. 13B illustrate an art drawing of the absence of the inhibitor o-NPA in the Biomimetic FGFR1 system, it has more interactions with the receptors of FGFR1.

Example 3

Human Cancer Cell Line MDA-MB-231

Figure 14:
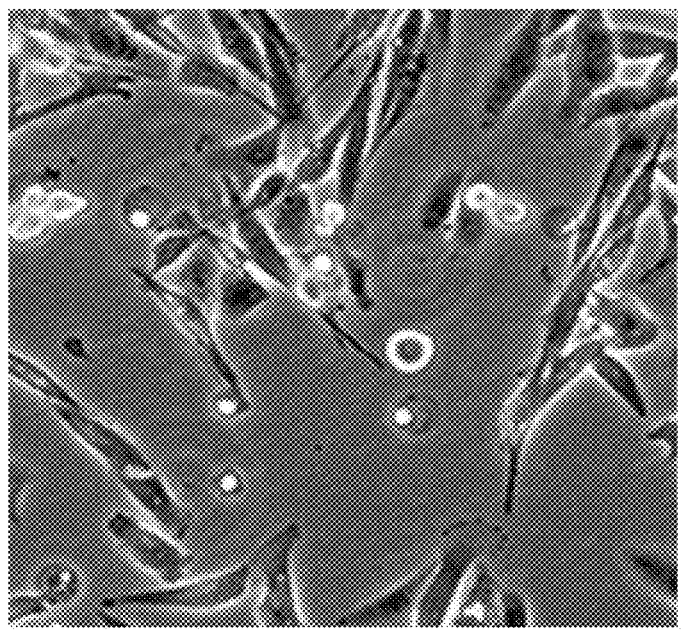
FIG. 14 is the image of the human breast cancer cells MDA-MB-231 in a base growing medium of DMEM (Dulbecco/Vogt Modified Eagle's minimal essential Medium—a common growth culture medium used for human cell incubation) infused with a 10% concentration of FBS (fetal bovine serum). It is kept in a normal atmosphere at a temperature of 37.0 degrees C. with $CO_2$.

Breast cancer cell samples are human adenocarcinoma cells taken from breast tissue. The cell cultures are held in a base growing medium of DMEM (Dulbecco/Vogt Modified Eagle's minimal essential Medium—a common growth culture medium used for human cell incubation) infused with a 10% concentration of FBS (fetal bovine serum). It contains 4.5 g/L glucose, sodium bicarbonate 1.5 g/L and L-glutamine 4 mM It is kept in a normal atmosphere at a temperature of 37.0 degrees C. with 10% $CO_2$. The culture requires medium renewal 2-3 times per week. The cancer cell lines and culture media were gifts from Germantown Innovation Center Dr. Y. Lee. The cancer cells in the DMEM media were 100 k cell/mL with or without incubation as shown in low cell density in FIG. 14. The incubation cell samples were incubated for 24 hrs in $CO_2$. Before test the cancer cells, a dilution procedure were conducted by diluting the high concentrated cell solution with the culture media. Hence beast cancer cell concentrations of 1, 5, 50, 100 and 200 cell/mL were prepared.

Example 4

Biomimetic Tyrosine Kinase Domain of FGFR1 Sensor as a NanobarCode Platform

The conventional method to study the cell signaling and the neuron activities is to measure the cell action potential and the resting potential to against the normal cell standard action and resting potential in order to discover the abnormal event or cause, such as drug abuse, brain injury or cancer. This method has drawbacks of low sensitivity and time consuming. Here the biomimetic tyrosine kinase domain of FGFR1 sensors as a nanobarcode model for antibody free direct detect cancer is presented. Here the living cell membrane action and resting potential concept in cell biology is transformed to a sensor system that is a unit of the FGFR1 sensor model complexes with cancer cells or neurons to form a battery that is a spontaneous energy device for discharge, i.e., conducts "action potential" and for a none spontaneous manner of taking a charge, i.e., "resting potential" activity in the membrane. The predicted benefits will be the single cancer cell action and resting potential can be sensitively detected without using antibody or labeling. It is well known enhanced protein tyrosine kinase (PTK) activity due to activating mutations of over expression has been implicated in many types of cancers [Reference 7-8] if without a powerful inhibitor. In another words, any cancerous cells enter the cavity of the Biomimetic FGFR1 sensor membrane network, will have a significant signal produced from the cancer cell's receptors interacts with the sensor receptor, or from some hydrophobic, hydrophilic, and hydrogen binding interaction without the presence of an inhibitor, this current invention has invented o-nitrophenyl acetate (NPA) as the inhibitor, because o-NPA has strong binding power to form an electron-relay system between the active sites of the polymer network and the receptors [9-10]. That event will be reflected a change of action potential and resting potential compared with or without o-NPA in the presence or absence of a cancer cell as shown in FIGS. 13A and B.

As for a comparison, an Au/PVP/PEG/mM-β-DMCD (see E. T. Chen. *Amperometric biomimetic enzyme sensors based on modified cyclodextrin as electrocatalysts*, and U.S. Pat. No. 6,582,583 issued on Jun. 24, 2003, and E. T. Chen. Nanopore Structured Electrochemical Biosensors, U.S. patent application Ser. No. 11/785,660 on Apr. 28, 2007, both of which are hereby incorporated by reference in entirety as if set forth herein), nanopore sensor will be used to validate the Au/TCD/PEG/co-polymer sensor.

Example 5

Effect of the Inhibitor o-NPA

Figure 15B:
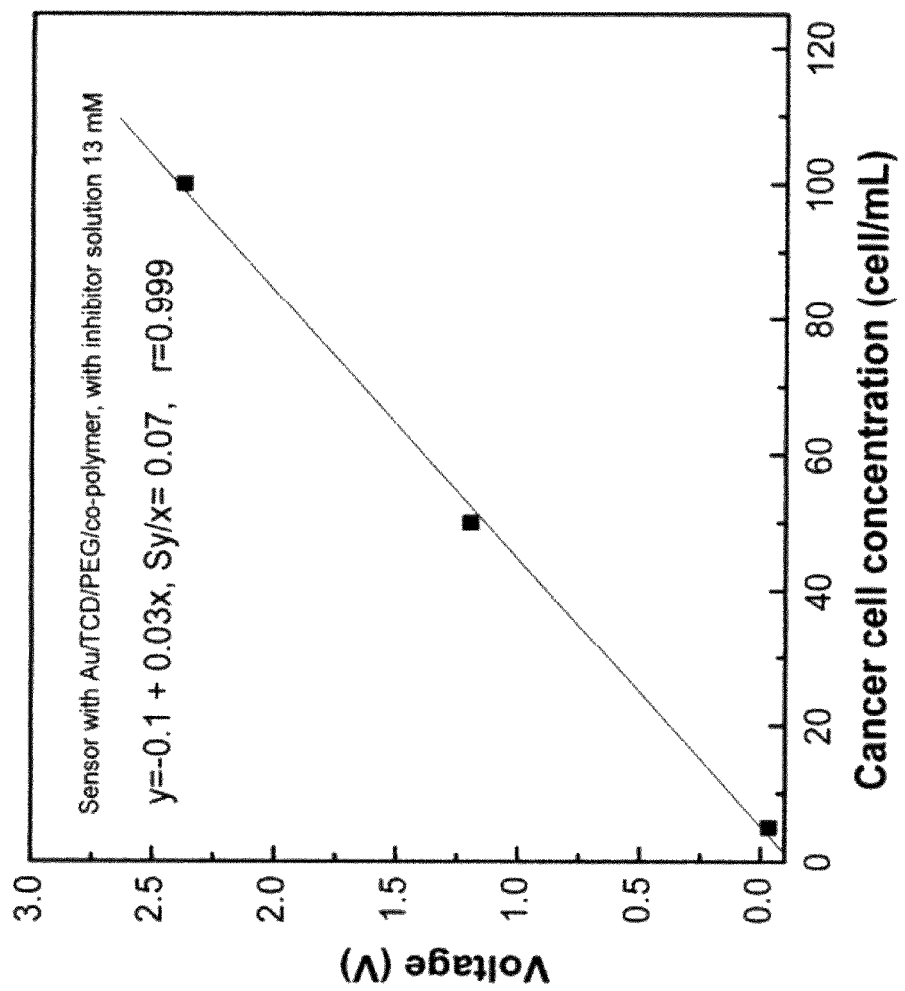
FIG. 15b illustrates the calibration curve of breast cancer cell concentration vs. the membrane action potential over 5 to 100 cell/mL range.

FIG. 15A demonstrated the Au/TCD/PEG/co-polymer sensor increased action potential from 0.18 V to 10 V that is a 55-fold increase in the absence of inhibitor o-NPA against that of with o-NPA with 5 breast cancer cells/mL detected by a double chronopotentiometry (DSCPO) method. It is also shown the behavior profiles of the breast cancer cells under inhibitor effect, how the cell concentration increase reflected the potential increase from 5, 50 to 100 cells/mL under 10 mA load. FIG. 15B is the linear regression plot of action potential vs. cancer cell concentration. It produced a linear line of y (V)=−0.1 (V)+0.03 (V/cell. $mL^{-1}$)x, Sy/x=0.07, r=0.999. Even under inhibition, the TCD sensor sensitivity for detecting cancer cell is 30 mv/cell. $mL^{-1}$ with the linear range up to 100 cell/mL. And the sensitivity for without inhibition is 2V/cell.$mL^{-1}$, which provided a valuable evidence that the platform can quantitatively detect a single cancer cell level with high sensitivity as we have predicted.

Figure 16A:
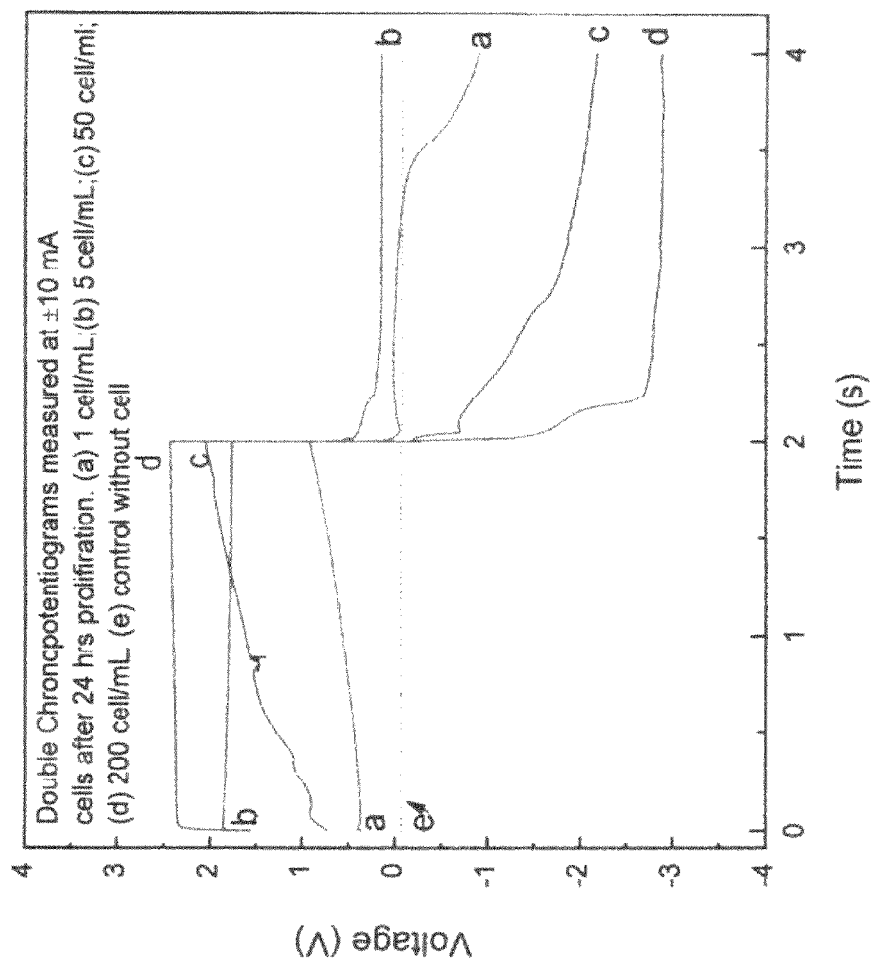
FIG. 16A illustrates the effect of cell concentration on the sensor Au/MCD/PEG/PVP performance using double chronopotentiometry method in the presence of 1, 5, 50 and 200 living breast cancer cells/mL without o-NPA from line (a to d) at ±10 mA after 24 hrs incubation against a negative control culture solution as the dotted line (e) under the same experimental conditions.
Figure 16B:
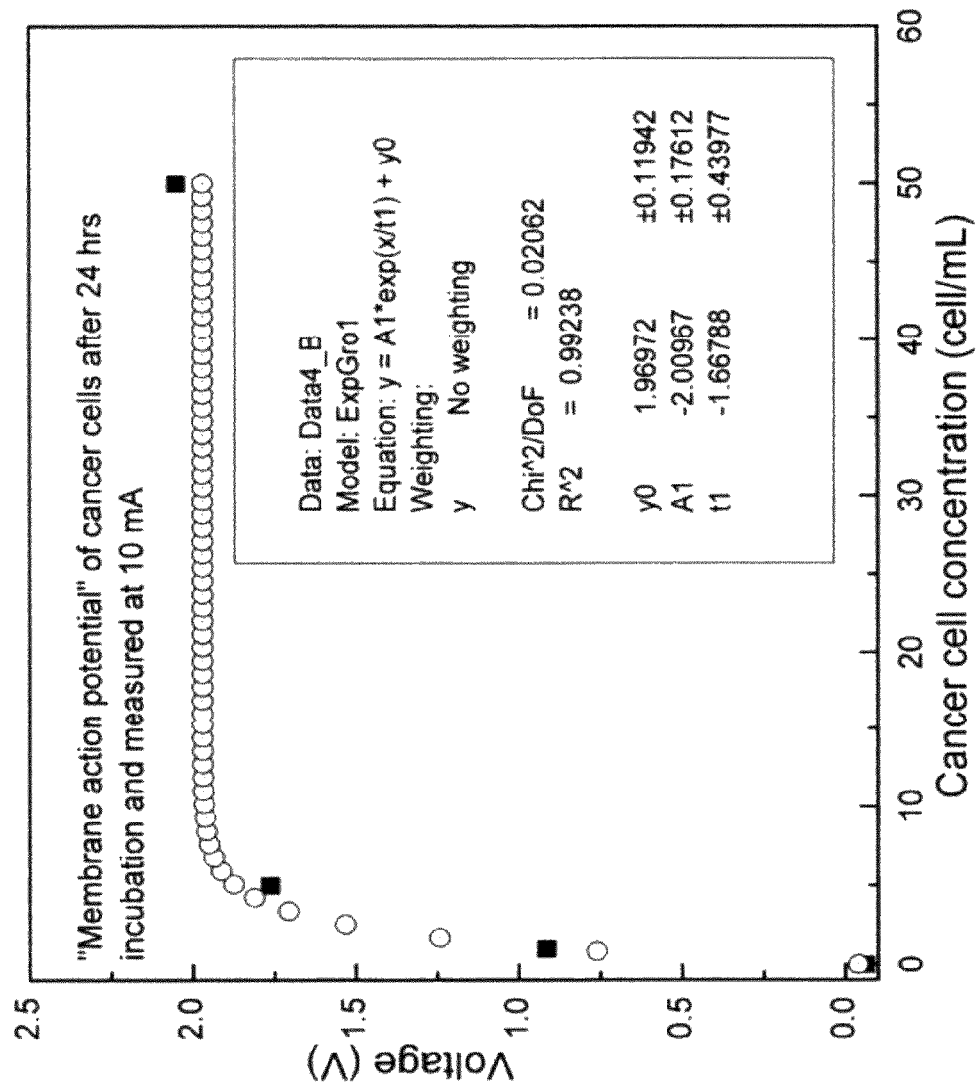
FIG. 16b illustrates the exponential growth curve of action potential of the membrane vs. the cell concentration. The open circles represent the fitting curve and the solid squares represent the experimental data.

In contrast, the Au/mM-β-DMCD/PEG/PVP sensor (MCD sensor) with 20 nm pores (FIG. 1) has ⅕ performance as compared with the Au/TCD/PEG/Co-polymer sensor even with 24 hrs incubation (FIG. 16A) under the same 10 mA load condition, indicating the MCD glucose sensor as a platform may not be the best for multiplex biomarker detection. FIG. 16B is the plot of action potential vs. cancer cell concentration for the MCD sensor without o-NPA after 24 hrs incubation and the curve fitting with the open circles represents the exponential first order model over the range 1 to 50 cell/mL. It has a 0.53V/cell. $mL^{-1}$ rate constant, which is 4-fold less than that of the TCD sensor without o-NPA.

Example 6

The Effect of the Current on the Action Potential Profiles

Figure 17:
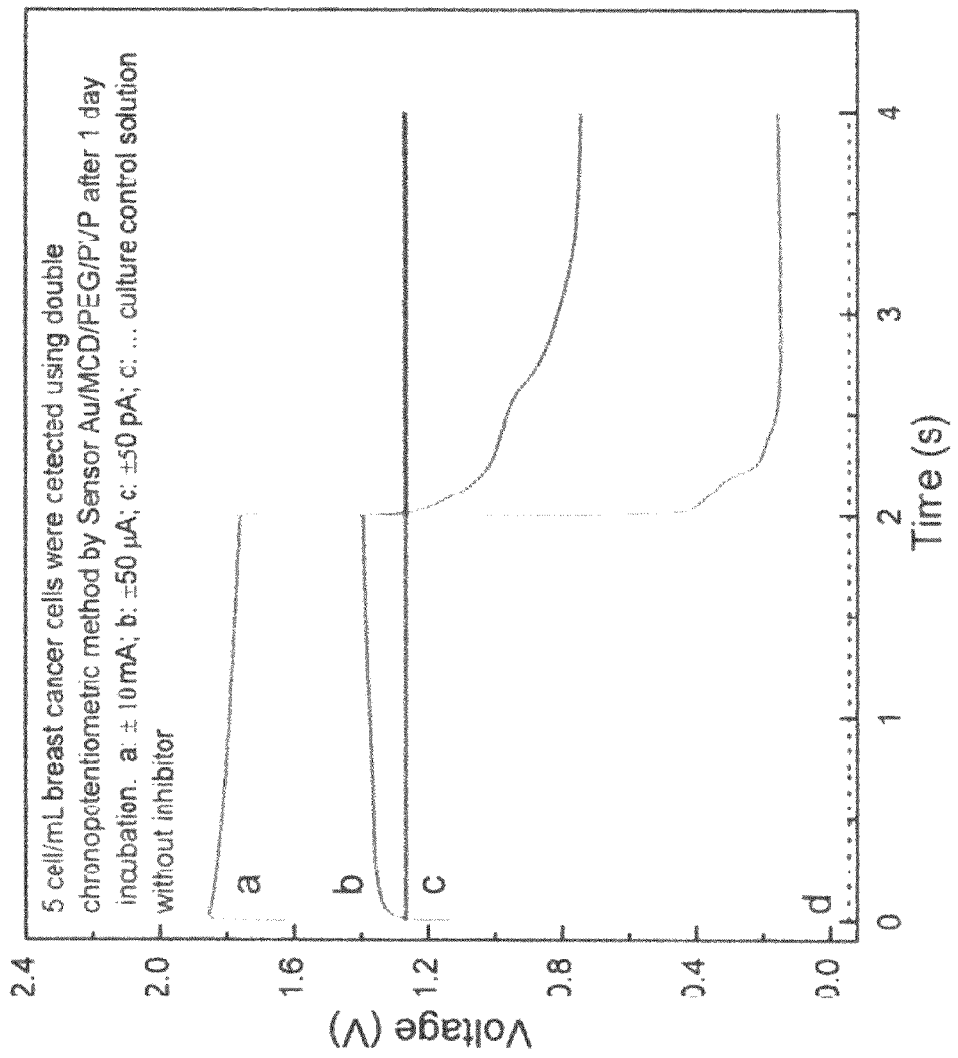
FIG. 17 illustrates sensor Au/MCD/PEG/PVP double chronopotentiometric profiles after 5 cell/mL 24 hrs incubation at 37° C. with 10% $CO_2$ at ±10 mA (a); ±50 µA (b); ±50 pA (c); against a negative control culture solution dotted line (d) under the same experimental conditions.
Figure 18:
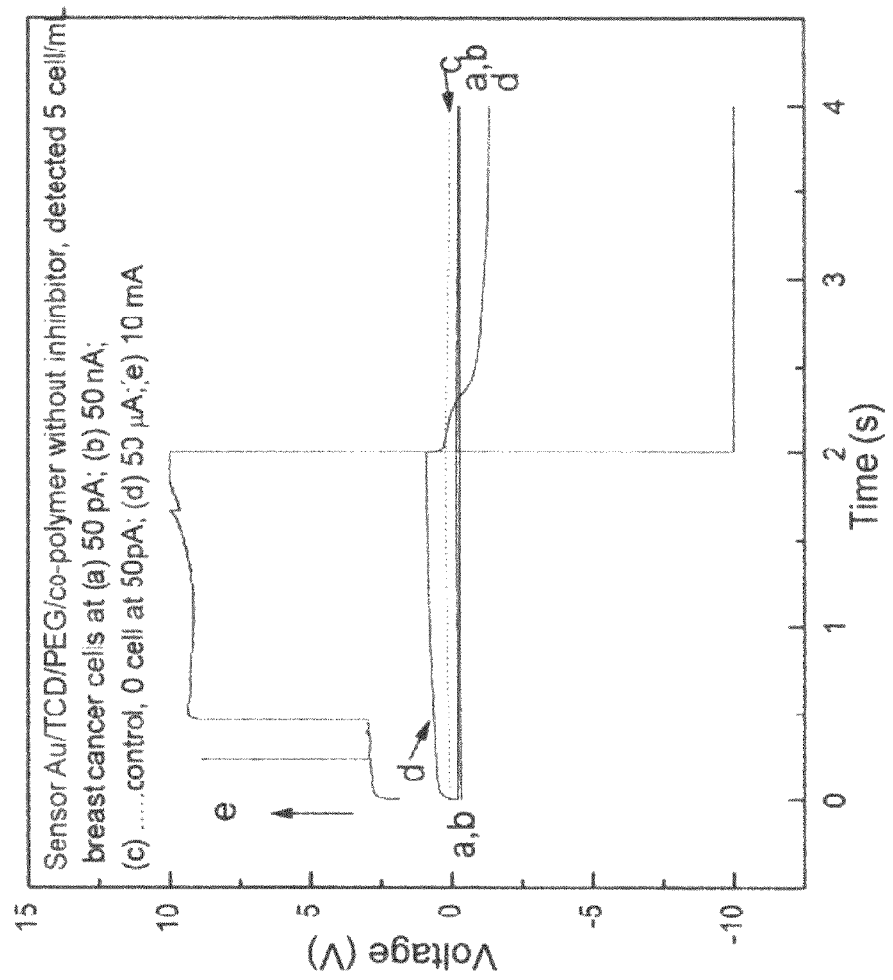
FIG. 18 illustrates 5 cell/mL breast cancer cells double chronopotentiometric profiles on sensor Au/TCD/PEG/co-polymer without inhibitor and without incubation at (a) 50 pA; (b) 50 nA; (c) . . . control; (d) 50 µA; (e) 10 mA

FIG. 17 illustrates the effect of current on sensor Au/mM-β-DMCD/PEG/PVP double chronopotentiometric profiles under a 5 cell/mL 24 hrs incubation without o-NPA at 37° C. with 10% $CO_2$ from ±10 mA, ±50 μA to ±50 μA against a negative control culture solution dotted line under the same experimental conditions, that were compared with sensor Au/TCD/PEG/co-polymer in FIG. 18. FIG. 18 illustrates 5 cell/mL breast cancer cells DSCPO profiles without inhibitor and without incubation from ±10 mA, ±50 μA, ±50 nA to ±50 pA against the negative control. The conclusion is that both sensors demonstrated the action potential increases as current increase with a fixed cancer cells. The TCD sensor has a magnitude higher increase rate than that of the MCD sensor at higher current (10 mA). Both sensors had significant potential increase at all current level compared with the negative control.

Example 7

Comparison Performance at Extreme Low Current

Figure 19A:
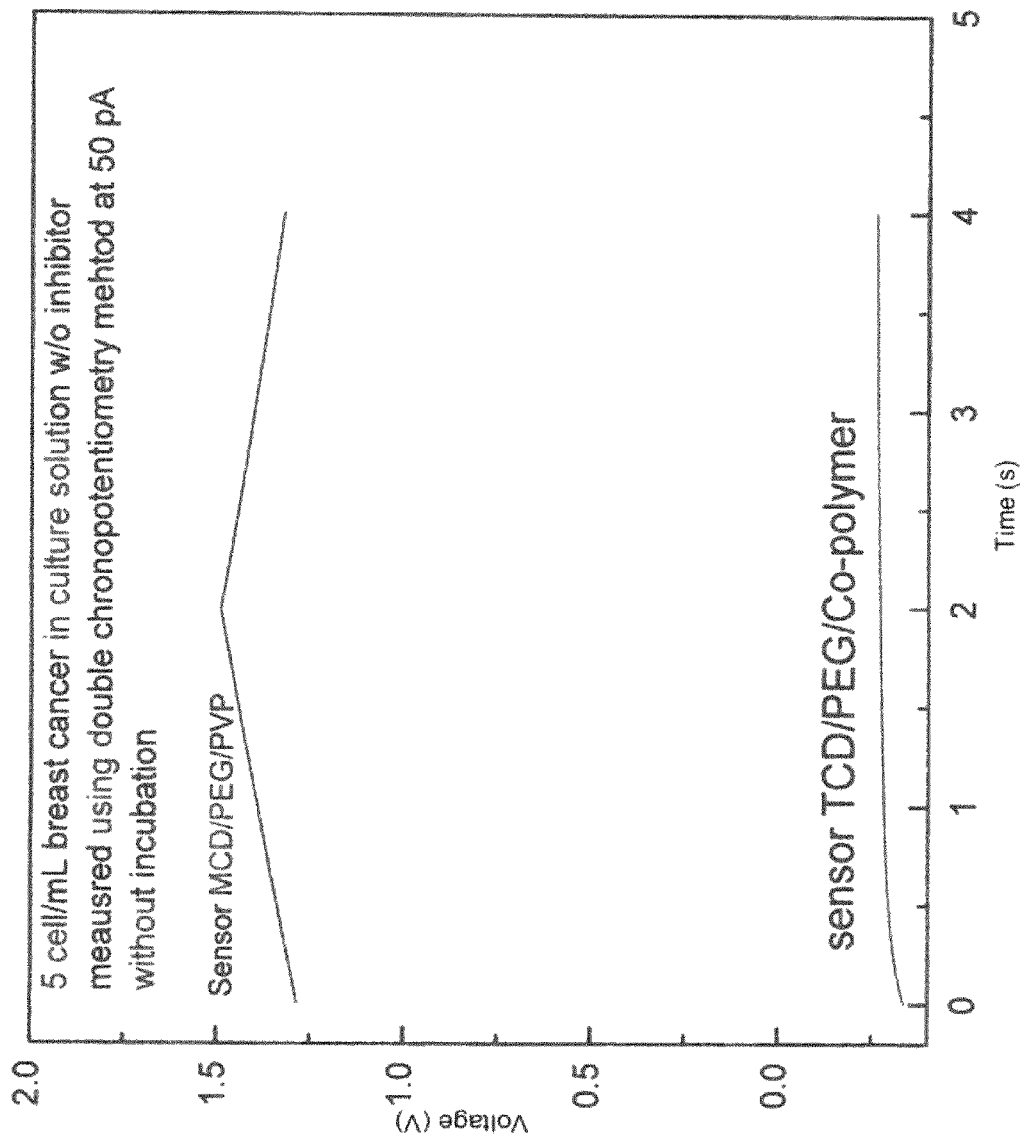
FIG. 19A illustrates the comparison of sensor performance between Au/TCD/PEG/Co-polymer and Au MCD/PEG/PVP on 5 cell/mL breast cancer w/o inhibitor using double chronopotentiometry method at 50 pA without incubation.
Figure 19B:
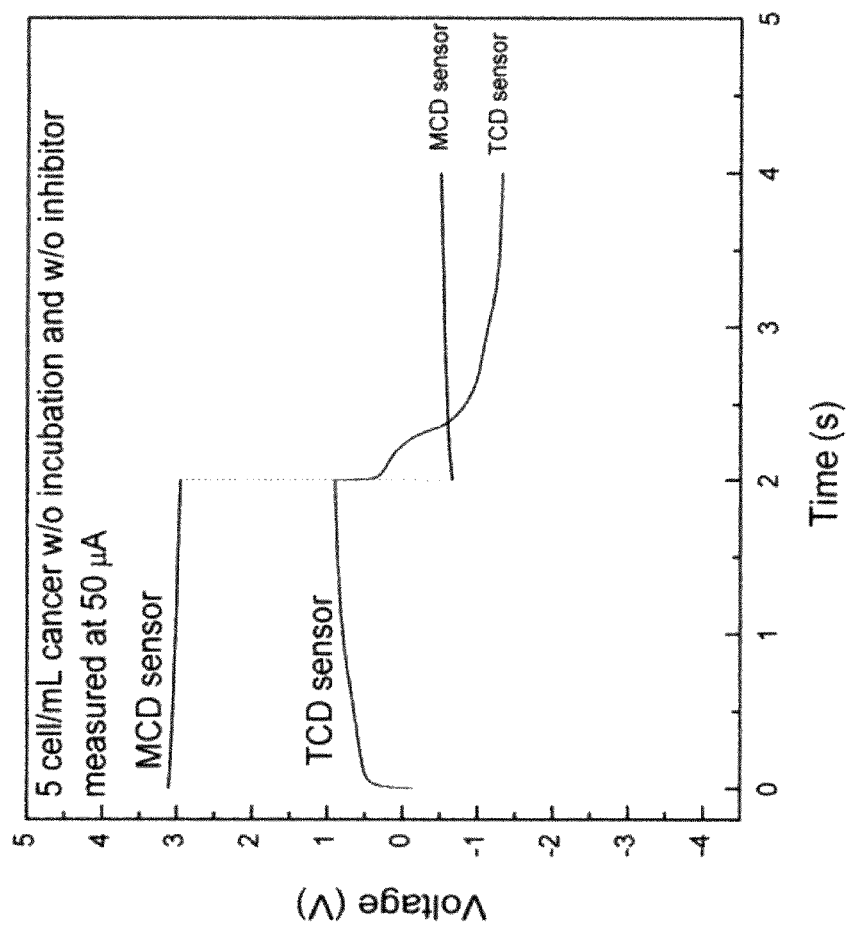
FIG. 19B illustrates the comparison of sensor performance between Au/TCD/PEG/Co-polymer and Au MCD/PEG/PVP on 5 cell/mL breast cancer w/o inhibitor using double chronopotentiometry method at 50 µA without incubation.

FIGS. 19 A and B illustrate the performance comparison of two types of sensors under no inhibitor and without incubation condition with cancer 5 cell/mL shown the MCD sensor is more sensitive at very low 50 pA current than TCD, that explains not only the small 20 nm pore size of MCD sensor offered advantage, but also the build in His-516 receptor has responded when current is low in pA range; when current increases, the TCD sensor will fast catch up that shows the advantage of not only the big 40 nm pore size, but also the receptor interactions between cancel cell and the sensor in the active sites.

Example 8

Chronoamperometric (CA) Profiles

FIG. 20 illustrates the typical chronoamperometric profiles of sensor Au/mM-β-DMCD/PEG/PVP with or without breast cancer cells after 24 hrs incubation in cultural media without o-NPA from 1 cell/mL to 100 cell/mL under appE1 −200 mV and appE2 −400 mV with step 60 ms. It generates a linear regression equation of y=0.4+0.08x, r=0.995, Sy/x=0.46 over the range 1-100 cell/mL with the sensitivity of 80 μA/cell.$mL^{-1}$.

Figure 21:
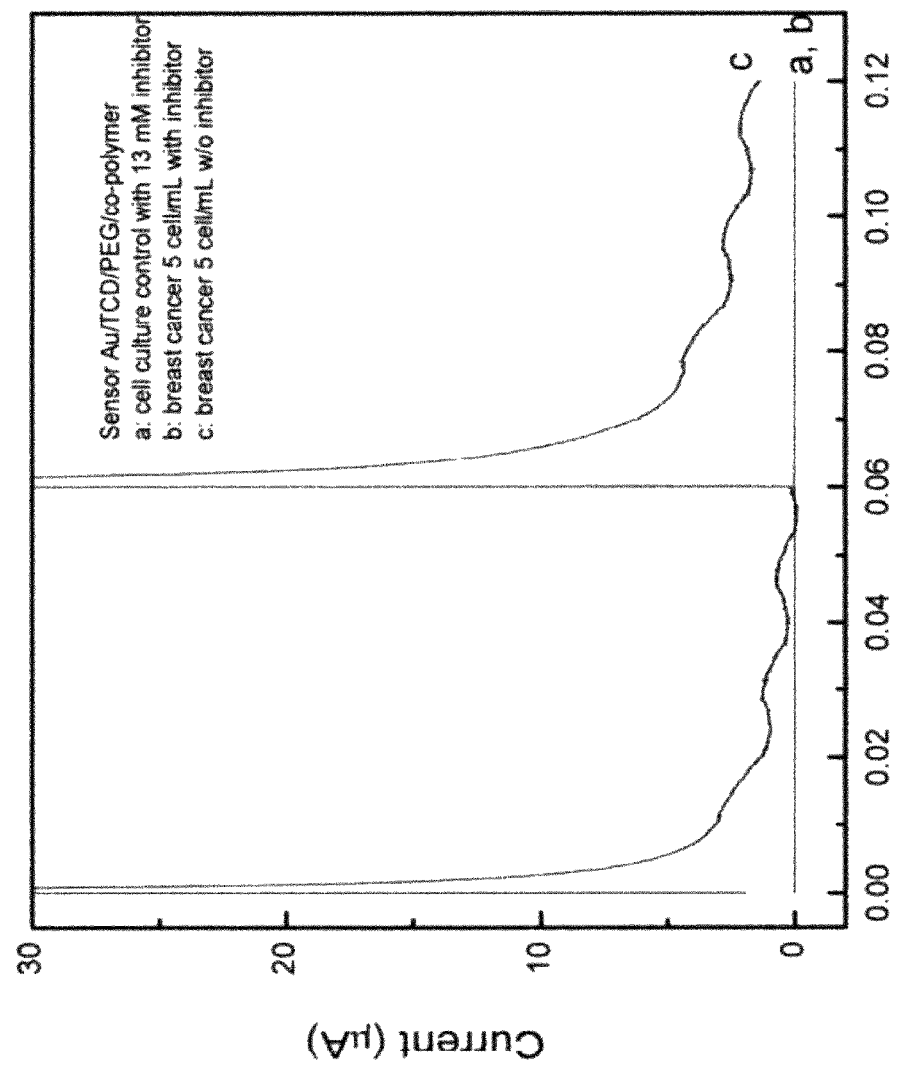
FIG. 21 illustrates the effect of inhibitor o-NPA on chronoamperometric profiles of sensor Au/TCD/PEG/co-polymer with or without breast cancer cells without incubation in cultural media (a) control, 0 cell, with o-NPA; (b) 5 cell/mL with o-NPA; (c) 5 cell/mL without inhibitor under the same experiment conditions as FIG. 20.

FIG. 21 illustrates the effect of inhibitor o-NPA on chronoamperometric profiles of sensor Au/TCD/PEG/co-polymer with or without breast cancer cells without incubation in cultural media (a) control, 0 cell, with o-NPA; (b) 5 cell/mL with o-NPA; (c) 5 cell/mL without inhibitor.

Example 9

Prototype Designs

Figure 22A:
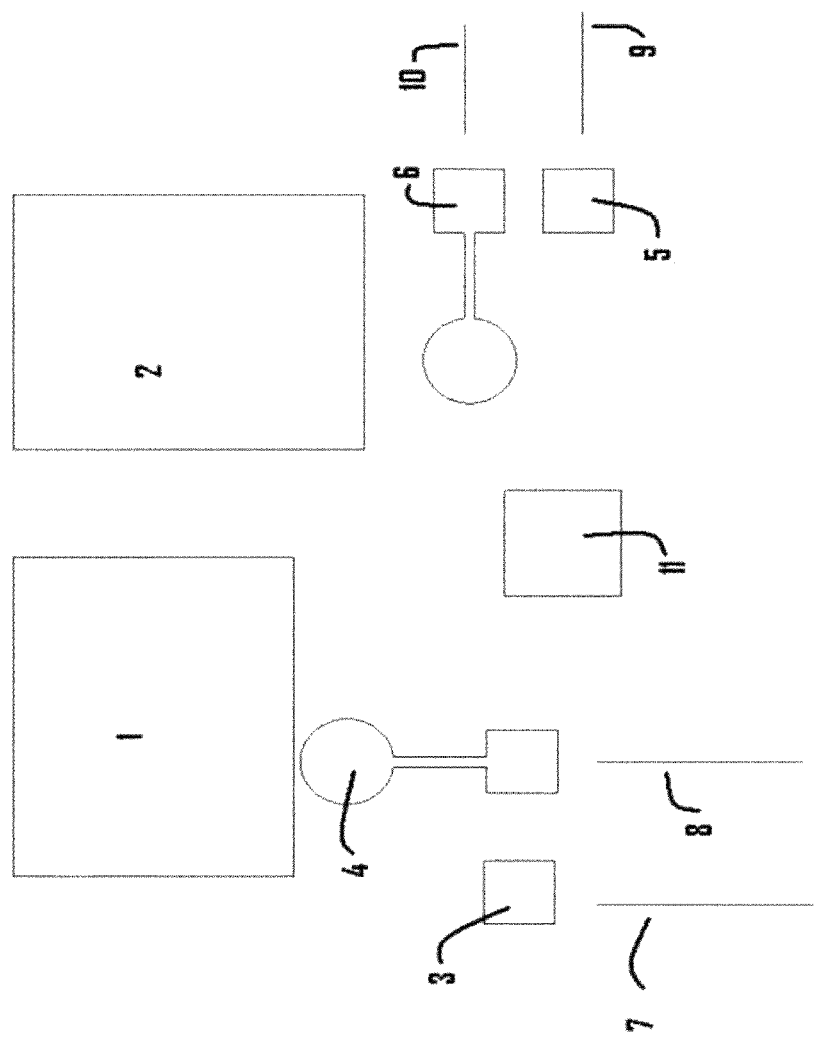
FIG. 22-a Illustrates a top-down, two-dimensional view of the v-shaped sensor and its numbered components.
Figure 22C:
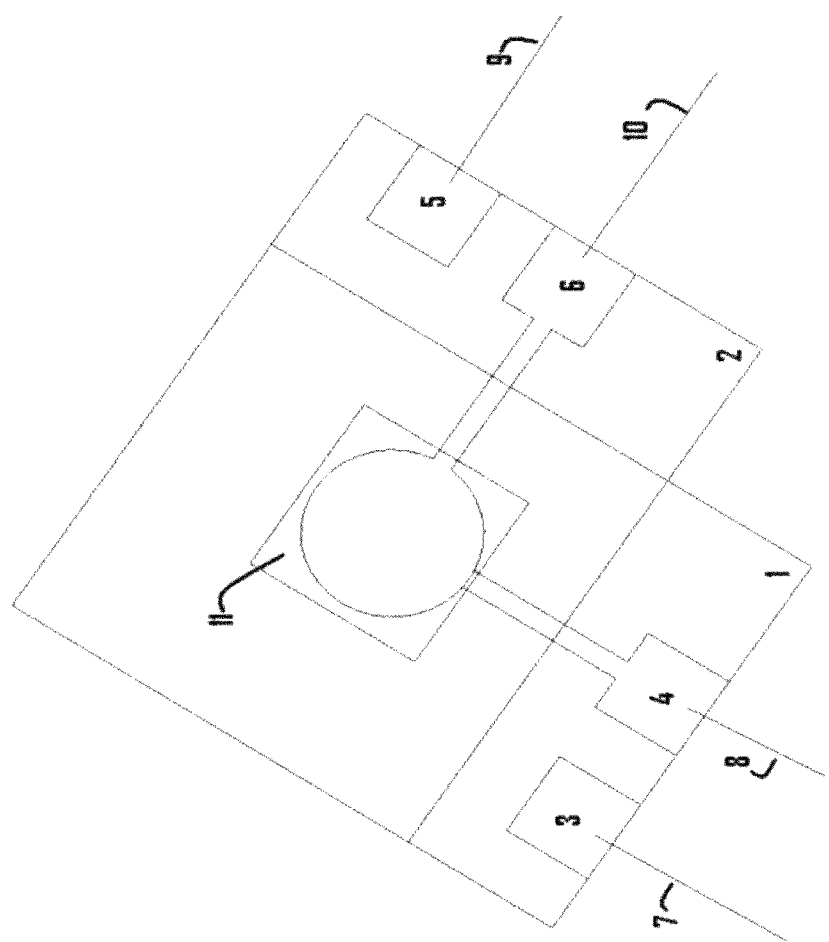
Figure 23:
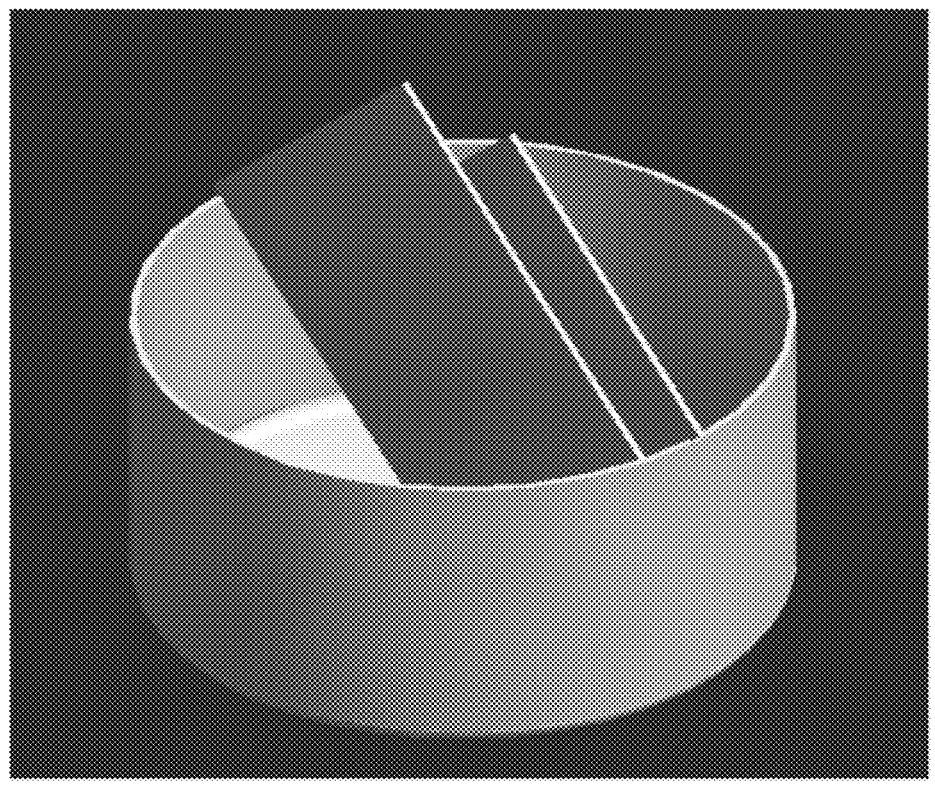
FIG. 23 Illustrates a 3 dimensional view of how the v-shaped sensor would be placed inside a well for testing.

FIGS. 22-*a*, 22-*b*, and 22-*c* illustrate 2-dimensional views of the v-shaped sensor design. FIG. 22-*a* depicts a view of the components that make up the sensor. FIG. 22-*b* shows how those components fit onto the working pieces of the component. FIG. 22-*c* shows how the parts come together and form the prototype. FIG. 23 also illustrates the v-shaped sensor but in a 3-dimensional view and in the context of how the sensor would sit in a well during testing.

Figure 24A:
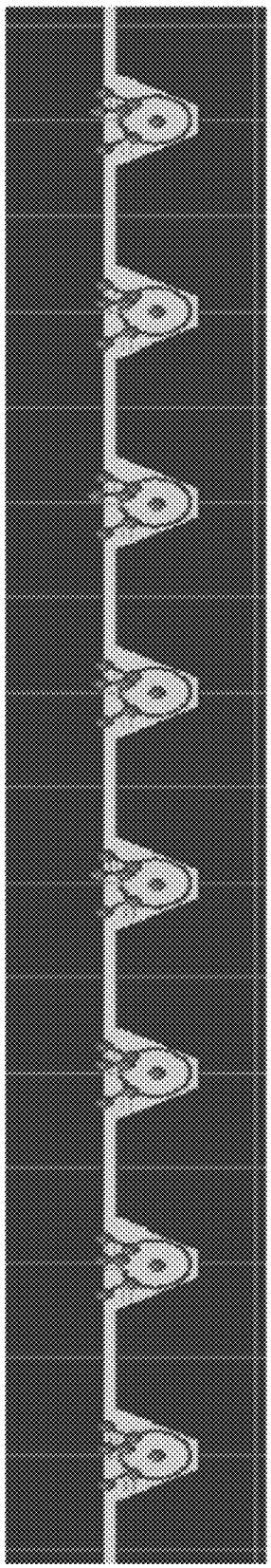
FIG. 24-a Illustrates a front-facing view of the prototype redesigns which allowed for multiple simultaneous testing.
Figure 24B:
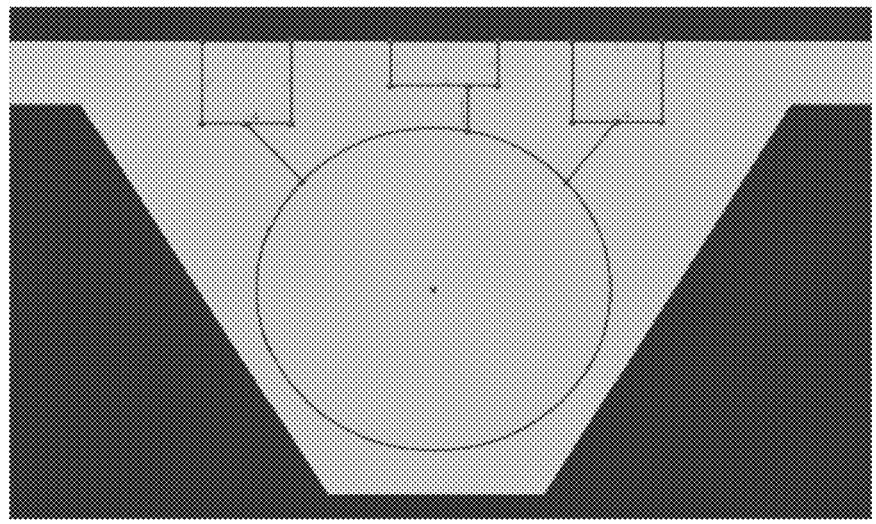
Figure 24C:
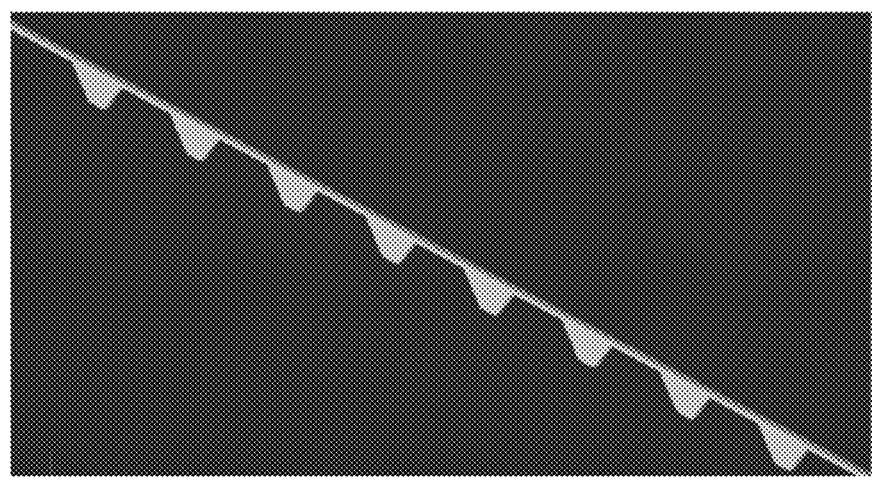

FIGS. 24-*a*, 24-*b*, and 24-*c* show the redesign of the v-shaped sensor to allow for more efficient and expedient testing. The original v-shaped design was cut at the bottom corner for increased sensor immersion into a solution well. The design was then replicated 8-fold for mass testing.

The invention claimed is:

1. A direct cell detecting device comprising:
   (a) an electrode comprising a substrate of gold;
   (b) a self-assembling membrane comprising of a polymer matrix comprised of an electrically conductive copolymer; wherein the copolymer is further comprised of:
      one or more first β-cyclodextrin molecules having at least one or more acetyl groups;
      and one or more polyethylene glycol molecules;
      and one or more second β-cyclodextrin molecules;
   wherein the self-assembling membrane has nanobiomimetic surface structure comprising one or more nanopores;
   the nanopores are vertically oriented on the substrate to form a nanopore array;
   the self-assembling membrane is configured to communicate to a target cell in order to detect a target cell concentration.

2. The direct cell detecting device according to claim 1, wherein the nanopores are independent and isolated from each other.

3. The direct cell detecting device according to claim 2, wherein the nanopores are uniform with an average pore size of 40 nm and the surface smoothness value of rms 4.2 nm.

4. The direct cell detecting device according to claim 1, wherein the nanopore is an electronic amplifier.

5. The direct cell detecting device according to claim 1, wherein an opening of the nanopore cavity is characterized as circular by AFM cross-section Analysis.

6. The direct cell detecting device according to claim 1, wherein the device is configured to detect the cell as an electrochemical amperometric sensor when voltage is applied as well as configured to be an energy storage device by detecting potential changes as a constant current discharged from the device to the environment.

7. The direct cell detecting device according to claim 1, wherein the device is free from natural enzymes.

8. The direct cell detecting device according to claim 1, wherein the device's function is free from antibody immune-binding.

9. The direct cell detecting device according to claim 1, wherein the device is free from mediator and labeling.

10. The direct cell detecting device according to claim 1, wherein the device is free from electrolyte interference.

11. The direct cell detecting device according to claim 1, wherein the device is free from oxygen interference.

12. The direct cell detecting device according to claim 1, wherein the device has sensitivity to detect cancer cells at $\pm 2$V/cell.mL$^{-1}$ at the action and resting potential respectively without the presence of an inhibitor and without incubation; And 30 mV/cell.mL$^{-1}$ from 5 cell/mL up to 100 cell/mL range to detect the cancer with an inhibitor, without incubation.

13. The direct cell detecting device according to claim 1, wherein the device has sensitivity as an amperometric sensor to detect 5 cancer cells/mL at 0.4 µA/cell.mL$^{-1}$ without an inhibitor and without incubation.

14. The direct cell detecting device according to claim 1, wherein the device further comprises an inhibitor, o-NPA, wherein the inhibitor is configured to completely block bio communication between the cell and the device.

15. The direct cell detecting device according to claim 14, wherein the inhibitor o-NPA has a concentration range between 8-15 mM.

16. The direct cell detecting device according to claim 1, wherein the device has a bioselectivity to be bioelectro-communicational to a living single breast cancer cell.

17. The direct cell detecting device according to claim 1, wherein the device has biological cell-to-cell recognition that prefers a binding of FGFR1 like protein over others from a living cancer cell.

18. The direct cell detecting device according to claim 1, wherein the device is configured to bio-communicate through the nanopore of the membrane and a nuclear pore of the cell in which the sizes of the membrane core and nuclear core are matched.

19. The direct cell detecting device according to claim 1, wherein the device consumes energy between 0.1-100 nW.

* * * * *